US011135054B2

(12) United States Patent
Nitzan et al.

(10) Patent No.: US 11,135,054 B2
(45) Date of Patent: *Oct. 5, 2021

(54) INTERATRIAL SHUNTS HAVING BIODEGRADABLE MATERIAL, AND METHODS OF MAKING AND USING SAME

(71) Applicant: V-Wave Ltd., Caesarea (IL)

(72) Inventors: Yaacov Nitzan, Hertzelia (IL); Menashe Yacoby, Ramat Gan (IL); Neal Eigler, Malibu, CA (US); James Whiting, Los Angeles, CA (US); Erez Rozenfeld, Shoham (IL)

(73) Assignee: V-Wave Ltd., Caesarea (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/395,209

(22) Filed: Apr. 25, 2019

(65) Prior Publication Data

US 2019/0254814 A1 Aug. 22, 2019

Related U.S. Application Data

(63) Continuation-in-part of application No. 15/492,852, filed on Apr. 20, 2017, now Pat. No. 10,368,981, (Continued)

(51) Int. Cl.
*A61F 2/24* (2006.01)
*A61B 17/00* (2006.01)
(Continued)

(52) U.S. Cl.
CPC ........ *A61F 2/2412* (2013.01); *A61B 17/0057* (2013.01); *A61F 2/2418* (2013.01);
(Continued)

(58) Field of Classification Search
CPC .................................. A61F 2/24; A61F 2/2412
See application file for complete search history.

(56) References Cited

U.S. PATENT DOCUMENTS 3,852,334 A 12/1974 Dusza et al.
3,874,388 A 4/1975 King et al.
(Continued)

FOREIGN PATENT DOCUMENTS

EP 2238933 A1 10/2010
EP 2305321 A1 4/2011
(Continued)

OTHER PUBLICATIONS

Ando et al., "Left ventricular decompression through a patent foramen ovale in a patient with hypertropic cardiomyopathy: A case report," Cardiovascular Ultrasound 2: 1-7 (2004).
(Continued)

*Primary Examiner* — Matthew W Schall
(74) *Attorney, Agent, or Firm* — Eversheds Sutherland (US) LLP; Christopher C. Bolten; Nicola A. Pisano

(57) ABSTRACT

A device for regulating blood pressure between a patient's left atrium and right atrium comprises an hourglass-shaped stent comprising a neck region and first and second flared end regions, the neck region disposed between the first and second end regions and configured to engage the fossa ovalis of the patient's atrial septum, and a drug-eluting biodegradable material that biodegrades over time to release a drug that limits tissue overgrowth. The inventive device also may include a biodegradable material that biodegrades to offset flow changes caused by tissue overgrowth. The inventive device may reduce left atrial pressure and left ventricular end diastolic pressure, and may increase cardiac output, increase ejection fraction, relieve pulmonary congestion, and lower pulmonary artery pressure, among other benefits.

25 Claims, 17 Drawing Sheets

Related U.S. Application Data which is a continuation of application No. 13/193,309, filed on Jul. 28, 2011, now Pat. No. 9,629,715.

(51) Int. Cl.
*A61F 2/90* (2013.01)
*A61F 2/966* (2013.01)

(52) U.S. Cl.
CPC ...... *A61F 2/90* (2013.01); *A61B 2017/00004* (2013.01); *A61B 2017/00243* (2013.01); *A61B 2017/00252* (2013.01); *A61B 2017/00592* (2013.01); *A61B 2017/00606* (2013.01); *A61B 2017/00623* (2013.01); *A61F 2/966* (2013.01); *A61F 2210/0004* (2013.01); *A61F 2230/001* (2013.01); *A61F 2250/0039* (2013.01); *A61F 2250/0067* (2013.01)

(56) References Cited

U.S. PATENT DOCUMENTS

| | | |
|---|---|---|
| 3,952,334 A | 4/1976 | Bokros et al. |
| 4,484,955 A | 11/1984 | Hochstein |
| 4,601,309 A | 7/1986 | Chang |
| 4,617,932 A | 10/1986 | Kornberg |
| 4,662,355 A | 5/1987 | Pieronne et al. |
| 4,665,906 A | 5/1987 | Jervis |
| 4,705,507 A | 11/1987 | Boyles |
| 4,836,204 A | 6/1989 | Landymore et al. |
| 4,979,955 A | 12/1990 | Smith |
| 4,988,339 A | 1/1991 | Vadher |
| 4,995,857 A | 2/1991 | Arnold |
| 5,035,706 A | 7/1991 | Giantureo et al. |
| 5,037,427 A | 8/1991 | Harada et al. |
| 5,089,005 A | 2/1992 | Harada |
| 5,186,431 A | 2/1993 | Tamari |
| 5,197,978 A | 3/1993 | Hess |
| 5,267,940 A | 12/1993 | Moulder |
| 5,290,227 A | 3/1994 | Pasque |
| 5,312,341 A | 5/1994 | Turi |
| 5,326,374 A | 7/1994 | Ilbawi et al. |
| 5,332,402 A | 7/1994 | Teitelbaum |
| 5,334,217 A | 8/1994 | Das |
| 5,378,239 A | 1/1995 | Termin et al. |
| 5,409,019 A | 4/1995 | Wilk |
| 5,429,144 A | 7/1995 | Wilk |
| 5,500,015 A | 3/1996 | Deac |
| 5,531,759 A | 7/1996 | Kensey et al. |
| 5,545,210 A | 8/1996 | Hess et al. |
| 5,556,386 A | 9/1996 | Todd |
| 5,578,008 A | 11/1996 | Hara |
| 5,584,803 A | 12/1996 | Stevens et al. |
| 5,597,377 A | 1/1997 | Aldea |
| 5,645,559 A | 7/1997 | Hachtman et al. |
| 5,655,548 A | 8/1997 | Nelson et al. |
| 5,662,711 A | 9/1997 | Douglas |
| 5,702,412 A | 12/1997 | Popov et al. |
| 5,725,552 A | 3/1998 | Kotula et al. |
| 5,741,324 A | 4/1998 | Glastra |
| 5,749,880 A | 5/1998 | Banas et al. |
| 5,779,716 A | 7/1998 | Cano et al. |
| 5,795,307 A | 8/1998 | Krueger |
| 5,810,836 A | 9/1998 | Hussein et al. |
| 5,824,062 A | 10/1998 | Patke et al. |
| 5,824,071 A | 10/1998 | Nelson et al. |
| 5,846,261 A | 12/1998 | Kotula et al. |
| 5,910,144 A | 6/1999 | Hayashi |
| 5,916,193 A | 6/1999 | Stevens et al. |
| 5,941,850 A | 8/1999 | Shah et al. |
| 5,957,949 A | 9/1999 | Leonhardt et al. |
| 5,990,379 A | 11/1999 | Gregory |
| 6,027,518 A | 2/2000 | Gaber |
| 6,039,755 A | 3/2000 | Edwin et al. |
| 6,039,759 A | 3/2000 | Carpentier et al. |
| 6,086,610 A | 7/2000 | Duerig et al. |
| 6,111,520 A | 8/2000 | Allen et al. |
| 6,117,159 A | 9/2000 | Huebsch et al. |
| 6,120,534 A | 9/2000 | Ruiz |
| 6,124,523 A | 9/2000 | Banas et al. |
| 6,126,686 A | 10/2000 | Badylak et al. |
| 6,165,188 A | 12/2000 | Saadat et al. |
| 6,210,318 B1 | 4/2001 | Lederman |
| 6,214,039 B1 | 4/2001 | Banas et al. |
| 6,217,541 B1 | 4/2001 | Yu |
| 6,221,096 B1 | 4/2001 | Aiba et al. |
| 6,242,762 B1 | 6/2001 | Brown et al. |
| 6,245,099 B1 | 6/2001 | Edwin et al. |
| 6,254,564 B1 | 7/2001 | Wilk et al. |
| 6,260,552 B1 | 7/2001 | Mortier et al. |
| 6,264,684 B1 | 7/2001 | Banas et al. |
| 6,270,515 B1 | 8/2001 | Linden et al. |
| 6,270,526 B1 | 8/2001 | Cox |
| 6,277,078 B1 | 8/2001 | Porat et al. |
| 6,278,379 B1 | 8/2001 | Allen et al. |
| 6,302,892 B1 | 10/2001 | Wilk |
| 6,306,141 B1 | 10/2001 | Jervis |
| 6,328,699 B1 | 12/2001 | Eigler et al. |
| 6,344,022 B1 | 2/2002 | Jarvik |
| 6,358,277 B1 | 3/2002 | Duran |
| 6,391,036 B1 | 5/2002 | Berg et al. |
| 6,398,803 B1 | 6/2002 | Layne et al. |
| 6,406,422 B1 | 6/2002 | Landesberg |
| 6,447,539 B1 | 9/2002 | Nelson et al. |
| 6,451,051 B2 | 9/2002 | Drasler et al. |
| 6,458,153 B1 | 10/2002 | Bailey et al. |
| 6,468,303 B1 | 10/2002 | Amplatz et al. |
| 6,475,136 B1 | 11/2002 | Forsell |
| 6,478,776 B1 | 11/2002 | Rosenman et al. |
| 6,485,507 B1 | 11/2002 | Walak et al. |
| 6,488,702 B1 | 12/2002 | Besselink |
| 6,491,705 B2 | 12/2002 | Gifford et al. |
| 6,527,698 B1 | 3/2003 | Kung et al. |
| 6,544,208 B2 | 4/2003 | Ethier et al. |
| 6,547,814 B2 | 4/2003 | Edwin et al. |
| 6,562,066 B1 | 5/2003 | Martin |
| 6,572,652 B2 | 6/2003 | Shaknovich |
| 6,579,314 B1 | 6/2003 | Lombardi et al. |
| 6,589,198 B1 | 7/2003 | Soltanpour et al. |
| 6,632,169 B2 | 10/2003 | Korakianitis et al. |
| 6,638,303 B1 | 10/2003 | Campbell |
| 6,641,610 B2 | 11/2003 | Wolf et al. |
| 6,652,578 B2 | 11/2003 | Bailey et al. |
| 6,685,664 B2 | 2/2004 | Levin et al. |
| 6,712,836 B1 | 3/2004 | Berg et al. |
| 6,740,115 B2 | 5/2004 | Lombardi et al. |
| 6,758,858 B2 | 7/2004 | McCrea et al. |
| 6,764,507 B2 | 7/2004 | Shanley et al. |
| 6,770,087 B2 | 8/2004 | Layne et al. |
| 6,797,217 B2 | 9/2004 | McCrea et al. |
| 6,890,350 B1 | 5/2005 | Walak |
| 6,970,742 B2 | 11/2005 | Mann et al. |
| 7,001,409 B2 | 2/2006 | Amplatz |
| 7,004,966 B2 | 2/2006 | Edwin et al. |
| 7,025,777 B2 | 4/2006 | Moore |
| 7,060,150 B2 | 6/2006 | Banas et al. |
| 7,083,640 B2 | 8/2006 | Lombardi et al. |
| 7,115,095 B2 | 10/2006 | Eigler et al. |
| 7,118,600 B2 | 10/2006 | Dua et al. |
| 7,137,953 B2 | 11/2006 | Eigler et al. |
| 7,147,604 B1 | 12/2006 | Allen et al. |
| 7,149,587 B2 | 12/2006 | Wardle et al. |
| 7,169,160 B1 | 1/2007 | Middleman et al. |
| 7,169,172 B2 | 1/2007 | Levine et al. |
| 7,195,594 B2 | 3/2007 | Eigler et al. |
| 7,208,010 B2 | 4/2007 | Shanley et al. |
| 7,226,558 B2 | 6/2007 | Nieman et al. |
| 7,245,117 B1 | 7/2007 | Joy et al. |
| 7,294,115 B1 | 11/2007 | Wilk |
| 7,306,756 B2 | 12/2007 | Edwin et al. |
| 7,402,899 B1 | 7/2008 | Whiting et al. |
| 7,439,723 B2 | 10/2008 | Allen et al. |
| 7,468,071 B2 | 12/2008 | Edwin et al. |
| 7,483,743 B2 | 1/2009 | Mann et al. |
| 7,498,799 B2 | 3/2009 | Allen et al. |

(56) References Cited

U.S. PATENT DOCUMENTS

| | | |
|---|---|---|
| 7,509,169 B2 | 3/2009 | Eigler et al. |
| 7,550,978 B2 | 6/2009 | Joy et al. |
| 7,578,899 B2 | 8/2009 | Edwin et al. |
| 7,590,449 B2 | 9/2009 | Mann et al. |
| 7,615,010 B1 | 11/2009 | Najafi et al. |
| 7,621,879 B2 | 11/2009 | Eigler et al. |
| 7,679,355 B2 | 3/2010 | Allen et al. |
| 7,717,854 B2 | 5/2010 | Mann et al. |
| 7,794,473 B2 | 9/2010 | Tessmer et al. |
| 7,839,153 B2 | 11/2010 | Joy et al. |
| 7,842,083 B2 | 11/2010 | Shanley et al. |
| 7,854,172 B2 | 12/2010 | O'Brien et al. |
| 7,862,513 B2 | 1/2011 | Eigler et al. |
| 7,914,639 B2 | 3/2011 | Layne et al. |
| 7,939,000 B2 | 5/2011 | Edwin et al. |
| 7,988,724 B2 | 8/2011 | Salahieh et al. |
| 7,993,383 B2 | 8/2011 | Hartley et al. |
| 8,012,194 B2 | 9/2011 | Edwin et al. |
| 8,016,877 B2 | 9/2011 | Seguin et al. |
| 8,021,420 B2 | 9/2011 | Dolan |
| 8,025,625 B2 | 9/2011 | Allen |
| 8,025,668 B2 | 9/2011 | McCartney |
| 8,043,360 B2 | 10/2011 | McNamara et al. |
| 8,070,708 B2 | 12/2011 | Rottenberg et al. |
| 8,091,556 B2 | 1/2012 | Keren et al. |
| 8,096,959 B2 | 1/2012 | Stewart et al. |
| 8,137,605 B2 | 3/2012 | McCrea et al. |
| 8,142,363 B1 | 3/2012 | Eigler et al. |
| 8,147,545 B2 | 4/2012 | Avior |
| 8,157,852 B2 | 4/2012 | Bloom et al. |
| 8,157,860 B2 | 4/2012 | McNamara et al. |
| 8,157,940 B2 | 4/2012 | Edwin et al. |
| 8,158,041 B2 | 4/2012 | Colone |
| 8,187,321 B2 | 5/2012 | Shanley et al. |
| 8,202,313 B2 | 6/2012 | Shanley et al. |
| 8,206,435 B2 | 6/2012 | Shanley et al. |
| 8,235,916 B2 | 8/2012 | Whiting et al. |
| 8,235,933 B2 | 8/2012 | Keren et al. |
| 8,246,677 B2 | 8/2012 | Ryan |
| 8,287,589 B2 | 10/2012 | Otto et al. |
| 8,298,150 B2 | 10/2012 | Mann et al. |
| 8,298,244 B2 | 10/2012 | Garcia et al. |
| 8,303,511 B2 | 11/2012 | Eigler et al. |
| 8,313,524 B2 | 11/2012 | Edwin et al. |
| 8,328,751 B2 | 12/2012 | Keren et al. |
| 8,337,650 B2 | 12/2012 | Edwin et al. |
| 8,348,996 B2 | 1/2013 | Tuval et al. |
| 8,357,193 B2 | 1/2013 | Phan et al. |
| 8,398,708 B2 | 3/2013 | Meiri et al. |
| 8,460,366 B2 | 6/2013 | Rowe |
| 8,468,667 B2 | 6/2013 | Straubinger et al. |
| 8,480,594 B2 | 7/2013 | Eigler et al. |
| 8,579,966 B2 | 11/2013 | Seguin et al. |
| 8,597,225 B2 | 12/2013 | Kapadia |
| 8,617,337 B2 | 12/2013 | Layne et al. |
| 8,617,441 B2 | 12/2013 | Edwin et al. |
| 8,652,284 B2 | 2/2014 | Bogert et al. |
| 8,665,086 B2 | 3/2014 | Miller et al. |
| 8,696,611 B2 | 4/2014 | Nitzan et al. |
| 8,790,241 B2 | 7/2014 | Edwin et al. |
| 8,882,697 B2 | 11/2014 | Celermajer et al. |
| 8,882,798 B2 | 11/2014 | Schwab et al. |
| 8,911,489 B2 | 12/2014 | Ben-Muvhar |
| 9,005,155 B2 | 4/2015 | Sugimoto |
| 9,034,034 B2 | 5/2015 | Nitzan et al. |
| 9,055,917 B2 | 6/2015 | Mann et al. |
| 9,060,696 B2 | 6/2015 | Eigler et al. |
| 9,067,050 B2 | 6/2015 | Gallagher et al. |
| 9,205,236 B2 | 12/2015 | McNamara et al. |
| 9,220,429 B2 | 12/2015 | Nabutovsky et al. |
| 9,358,371 B2 | 6/2016 | McNamara et al. |
| 9,393,115 B2 | 7/2016 | Tabor et al. |
| 9,456,812 B2 | 10/2016 | Finch et al. |
| 9,622,895 B2 | 4/2017 | Cohen et al. |
| 9,629,715 B2 | 4/2017 | Nitzan et al. |
| 9,681,948 B2 | 6/2017 | Levi et al. |
| 9,707,382 B2 | 7/2017 | Nitzan et al. |
| 9,713,696 B2 | 7/2017 | Yacoby et al. |
| 9,757,107 B2 | 9/2017 | McNamara et al. |
| 9,789,294 B2 | 10/2017 | Taft et al. |
| 9,918,677 B2 | 3/2018 | Eigler et al. |
| 9,943,670 B2 | 4/2018 | Keren et al. |
| 9,980,815 B2 | 5/2018 | Nitzan et al. |
| 10,045,766 B2 | 8/2018 | McNamara et al. |
| 10,047,421 B2 | 8/2018 | Khan et al. |
| 10,076,403 B1 | 9/2018 | Eigler et al. |
| 10,105,103 B2 | 10/2018 | Goldshtein et al. |
| 10,111,741 B2 | 10/2018 | Michalak |
| 10,207,087 B2 | 2/2019 | Keren et al. |
| 10,207,807 B2 | 2/2019 | Moran et al. |
| 10,251,740 B2 | 4/2019 | Eigler et al. |
| 10,251,750 B2 | 4/2019 | Eigler et al. |
| 10,299,687 B2 | 5/2019 | Nabutovsky et al. |
| 10,357,320 B2 | 7/2019 | Beira |
| 10,357,357 B2 | 7/2019 | Levi et al. |
| 10,368,981 B2 | 8/2019 | Nitzan et al. |
| 10,463,490 B2 | 11/2019 | Rottenberg et al. |
| 10,478,594 B2 | 11/2019 | Yacoby et al. |
| 10,548,725 B2 | 2/2020 | Alkhatib et al. |
| 10,561,423 B2 | 2/2020 | Sharma |
| 10,639,459 B2 | 5/2020 | Nitzan et al. |
| 2002/0120277 A1 | 8/2002 | Hauschild et al. |
| 2002/0165479 A1 | 11/2002 | Wilk |
| 2002/0165606 A1 | 11/2002 | Wolf et al. |
| 2002/0169371 A1 | 11/2002 | Gilderdale |
| 2002/0169377 A1 | 11/2002 | Khairkhahan et al. |
| 2002/0173742 A1 | 11/2002 | Keren et al. |
| 2003/0100920 A1 | 5/2003 | Akin et al. |
| 2003/0125798 A1 | 7/2003 | Martin |
| 2003/0136417 A1 | 7/2003 | Fonseca et al. |
| 2003/0176914 A1 | 9/2003 | Rabkin et al. |
| 2003/0209835 A1 | 11/2003 | Chun et al. |
| 2003/0216679 A1 | 11/2003 | Wolf et al. |
| 2003/0216803 A1 | 11/2003 | Ledergerber |
| 2004/0010219 A1 | 1/2004 | McCusker et al. |
| 2004/0016514 A1 | 1/2004 | Nien |
| 2004/0077988 A1 | 4/2004 | Tweden et al. |
| 2004/0088045 A1 | 5/2004 | Cox |
| 2004/0093075 A1 | 5/2004 | Kuehne |
| 2004/0102797 A1 | 5/2004 | Golden et al. |
| 2004/0116999 A1 | 6/2004 | Ledergerber |
| 2004/0138743 A1 | 7/2004 | Myers et al. |
| 2004/0147869 A1 | 7/2004 | Wolf et al. |
| 2004/0147871 A1 | 7/2004 | Burnett |
| 2004/0147886 A1 | 7/2004 | Bonni |
| 2004/0162514 A1 | 8/2004 | Alferness et al. |
| 2004/0193261 A1 | 9/2004 | Berreklouw |
| 2004/0210190 A1 | 10/2004 | Kohler et al. |
| 2004/0210307 A1 | 10/2004 | Khairkhahan |
| 2004/0225352 A1 | 11/2004 | Osborne et al. |
| 2005/0003327 A1 | 1/2005 | Elian et al. |
| 2005/0033327 A1 | 2/2005 | Gainor et al. |
| 2005/0033351 A1 | 2/2005 | Newton |
| 2005/0065589 A1 | 3/2005 | Schneider et al. |
| 2005/0137682 A1 | 6/2005 | Justino |
| 2005/0148925 A1 | 7/2005 | Rottenberg et al. |
| 2005/0165344 A1 | 7/2005 | Dobak, III |
| 2005/0182486 A1 | 8/2005 | Gabbay |
| 2005/0283231 A1 | 12/2005 | Haug et al. |
| 2006/0009800 A1 | 1/2006 | Christianson et al. |
| 2006/0025857 A1 | 2/2006 | Bergheim et al. |
| 2006/0111660 A1 | 5/2006 | Wolf et al. |
| 2006/0116710 A1 | 6/2006 | Corcoran et al. |
| 2006/0122647 A1 | 6/2006 | Callaghan et al. |
| 2006/0167541 A1 | 7/2006 | Lattouf |
| 2006/0184231 A1 | 8/2006 | Rucker |
| 2006/0212110 A1 | 9/2006 | Osborne et al. |
| 2006/0241745 A1 | 10/2006 | Solem |
| 2006/0256611 A1 | 11/2006 | Bednorz et al. |
| 2006/0282157 A1 | 12/2006 | Hill et al. |
| 2007/0010852 A1 | 1/2007 | Blaeser et al. |
| 2007/0021739 A1 | 1/2007 | Weber |
| 2007/0043435 A1 | 2/2007 | Seguin et al. |
| 2007/0191863 A1 | 8/2007 | De Juan, Jr. et al. |

(56) References Cited

U.S. PATENT DOCUMENTS

| | | |
|---|---|---|
| 2007/0213813 A1 | 9/2007 | Von Segesser et al. |
| 2007/0276413 A1 | 11/2007 | Nobles |
| 2007/0276414 A1 | 11/2007 | Nobles |
| 2007/0282157 A1 | 12/2007 | Rottenberg et al. |
| 2007/0299384 A1 | 12/2007 | Faul et al. |
| 2008/0034836 A1 | 2/2008 | Eigler et al. |
| 2008/0086205 A1 | 4/2008 | Gordy et al. |
| 2008/0125861 A1 | 5/2008 | Webler et al. |
| 2008/0177300 A1 | 7/2008 | Mas et al. |
| 2008/0262602 A1 | 10/2008 | Wilk et al. |
| 2008/0319525 A1 | 12/2008 | Tieu et al. |
| 2009/0030499 A1 | 1/2009 | Bebb et al. |
| 2009/0054976 A1 | 2/2009 | Tuval et al. |
| 2009/0125104 A1 | 5/2009 | Hoffman |
| 2009/0149947 A1 | 6/2009 | Frohwitter |
| 2009/0198315 A1 | 8/2009 | Boudjemline |
| 2009/0276040 A1 | 11/2009 | Rowe et al. |
| 2009/0319037 A1 | 12/2009 | Rowe et al. |
| 2010/0004740 A1 | 1/2010 | Seguin et al. |
| 2010/0022940 A1 | 1/2010 | Thompson |
| 2010/0057192 A1 | 3/2010 | Celermajer |
| 2010/0069836 A1 | 3/2010 | Satake |
| 2010/0070022 A1 | 3/2010 | Kuehling |
| 2010/0081867 A1 | 4/2010 | Fishler et al. |
| 2010/0100167 A1 | 4/2010 | Bortlein et al. |
| 2010/0121434 A1 | 5/2010 | Paul et al. |
| 2010/0179590 A1 | 7/2010 | Fortson et al. |
| 2010/0191326 A1 | 7/2010 | Alkhatib |
| 2010/0249909 A1 | 9/2010 | McNamara et al. |
| 2010/0249910 A1 | 9/2010 | McNamara et al. |
| 2010/0249915 A1 | 9/2010 | Zhang |
| 2010/0256548 A1 | 10/2010 | McNamara et al. |
| 2010/0256753 A1 | 10/2010 | McNamara et al. |
| 2010/0298755 A1 | 11/2010 | McNamara et al. |
| 2011/0022057 A1 | 1/2011 | Eigler et al. |
| 2011/0022157 A1 | 1/2011 | Essinger et al. |
| 2011/0054515 A1 | 3/2011 | Bridgeman et al. |
| 2011/0071623 A1 | 3/2011 | Finch et al. |
| 2011/0071624 A1 | 3/2011 | Finch et al. |
| 2011/0093059 A1 | 4/2011 | Fischell et al. |
| 2011/0152923 A1 | 6/2011 | Fox |
| 2011/0190874 A1 | 8/2011 | Celermajer et al. |
| 2011/0218479 A1 | 9/2011 | Rottenberg et al. |
| 2011/0218480 A1 | 9/2011 | Rottenberg et al. |
| 2011/0218481 A1 | 9/2011 | Rottenberg et al. |
| 2011/0257723 A1 | 10/2011 | McNamara |
| 2011/0264203 A1 | 10/2011 | Dwork et al. |
| 2011/0276086 A1 | 11/2011 | Al-Qbandi et al. |
| 2011/0295182 A1 | 12/2011 | Finch et al. |
| 2011/0295183 A1 | 12/2011 | Finch et al. |
| 2011/0295362 A1 | 12/2011 | Finch et al. |
| 2011/0295366 A1 | 12/2011 | Finch et al. |
| 2011/0306916 A1 | 12/2011 | Nitzan et al. |
| 2011/0319806 A1 | 12/2011 | Wardle |
| 2012/0022633 A1 | 1/2012 | Olson et al. |
| 2012/0035590 A1 | 2/2012 | Whiting et al. |
| 2012/0041422 A1 | 2/2012 | Whiting et al. |
| 2012/0046528 A1 | 2/2012 | Eigler et al. |
| 2012/0046739 A1 | 2/2012 | Von Oepen et al. |
| 2012/0053686 A1 | 3/2012 | McNamara et al. |
| 2012/0071918 A1 | 3/2012 | Amin et al. |
| 2012/0130301 A1 | 5/2012 | McNamara et al. |
| 2012/0165928 A1 | 6/2012 | Nitzan et al. |
| 2012/0179172 A1 | 7/2012 | Paul et al. |
| 2012/0190991 A1 | 7/2012 | Bornzin et al. |
| 2012/0265296 A1 | 10/2012 | McNamara et al. |
| 2012/0271398 A1 | 10/2012 | Essinger et al. |
| 2012/0289882 A1 | 11/2012 | McNamara et al. |
| 2012/0290062 A1 | 11/2012 | McNamara et al. |
| 2013/0030521 A1 | 1/2013 | Nitzan et al. |
| 2013/0046373 A1 | 2/2013 | Cartledge et al. |
| 2013/0138145 A1 | 5/2013 | Von Oepen |
| 2013/0178783 A1 | 7/2013 | McNamara et al. |
| 2013/0178784 A1 | 7/2013 | McNamara et al. |
| 2013/0184633 A1 | 7/2013 | McNamara et al. |
| 2013/0184634 A1 | 7/2013 | McNamara et al. |
| 2013/0197423 A1 | 8/2013 | Keren et al. |
| 2013/0197547 A1 | 8/2013 | Fukuoka et al. |
| 2013/0197629 A1 | 8/2013 | Gainor et al. |
| 2013/0204175 A1 | 8/2013 | Sugimoto |
| 2013/0231737 A1 | 9/2013 | McNamara et al. |
| 2013/0261531 A1 | 10/2013 | Gallagher et al. |
| 2013/0281988 A1 | 10/2013 | Magnin et al. |
| 2013/0304192 A1 | 11/2013 | Chanduszko |
| 2014/0012181 A1 | 1/2014 | Sugimoto et al. |
| 2014/0012303 A1 | 1/2014 | Heipl |
| 2014/0012368 A1 | 1/2014 | Sugimoto et al. |
| 2014/0012369 A1 | 1/2014 | Murry, III et al. |
| 2014/0067037 A1 | 3/2014 | Fargahi |
| 2014/0094904 A1 | 4/2014 | Salahieh et al. |
| 2014/0128795 A1 | 5/2014 | Keren et al. |
| 2014/0128796 A1 | 5/2014 | Keren et al. |
| 2014/0163449 A1 | 6/2014 | Rottenberg et al. |
| 2014/0194971 A1 | 7/2014 | McNamara |
| 2014/0213959 A1 | 7/2014 | Nitzan et al. |
| 2014/0222144 A1 | 8/2014 | Eberhardt et al. |
| 2014/0249621 A1 | 9/2014 | Eidenschink |
| 2014/0257167 A1 | 9/2014 | Celermajer |
| 2014/0275916 A1 | 9/2014 | Nabutovsky et al. |
| 2014/0277045 A1 | 9/2014 | Fazio et al. |
| 2014/0277054 A1 | 9/2014 | McNamara et al. |
| 2014/0303710 A1 | 10/2014 | Zhang et al. |
| 2014/0350565 A1 | 11/2014 | Yacoby et al. |
| 2014/0350658 A1 | 11/2014 | Benary et al. |
| 2014/0350661 A1 | 11/2014 | Schaeffer |
| 2014/0350669 A1 | 11/2014 | Gillespie et al. |
| 2014/0357946 A1 | 12/2014 | Golden et al. |
| 2015/0039084 A1 | 2/2015 | Levi et al. |
| 2015/0066140 A1 | 3/2015 | Quadri et al. |
| 2015/0073539 A1 | 3/2015 | Geiger et al. |
| 2015/0119796 A1 | 4/2015 | Finch |
| 2015/0127093 A1 | 5/2015 | Hosmer et al. |
| 2015/0142049 A1 | 5/2015 | Delgado et al. |
| 2015/0148731 A1 | 5/2015 | McNamara et al. |
| 2015/0148896 A1 | 5/2015 | Karapetian et al. |
| 2015/0157455 A1 | 6/2015 | Hoang et al. |
| 2015/0173897 A1 | 6/2015 | Raanani et al. |
| 2015/0182334 A1 | 7/2015 | Bourang et al. |
| 2015/0190229 A1 | 7/2015 | Seguin |
| 2015/0196383 A1 | 7/2015 | Johnson |
| 2015/0201998 A1 | 7/2015 | Roy et al. |
| 2015/0209143 A1 | 7/2015 | Duffy et al. |
| 2015/0230924 A1 | 8/2015 | Miller et al. |
| 2015/0238314 A1 | 8/2015 | Bortlein et al. |
| 2015/0245908 A1 | 9/2015 | Nitzan et al. |
| 2015/0272731 A1 | 10/2015 | Racchini et al. |
| 2015/0282790 A1 | 10/2015 | Quinn et al. |
| 2015/0282931 A1 | 10/2015 | Brunnett et al. |
| 2015/0359556 A1 | 12/2015 | Vardi |
| 2016/0007924 A1 | 1/2016 | Eigler et al. |
| 2016/0022423 A1 | 1/2016 | McNamara et al. |
| 2016/0022970 A1 | 1/2016 | Forcucci et al. |
| 2016/0073907 A1 | 3/2016 | Nabutovsky et al. |
| 2016/0120550 A1 | 5/2016 | McNamara et al. |
| 2016/0129260 A1 | 5/2016 | Mann et al. |
| 2016/0157862 A1 | 6/2016 | Hernandez et al. |
| 2016/0166381 A1 | 6/2016 | Sugimoto et al. |
| 2016/0184561 A9 | 6/2016 | McNamara et al. |
| 2016/0206423 A1 | 7/2016 | O'Connor et al. |
| 2016/0213467 A1 | 7/2016 | Backus et al. |
| 2016/0220360 A1 | 8/2016 | Lin et al. |
| 2016/0220365 A1 | 8/2016 | Backus et al. |
| 2016/0262878 A1 | 9/2016 | Backus et al. |
| 2016/0262879 A1 | 9/2016 | Meiri et al. |
| 2016/0287386 A1 | 10/2016 | Alon et al. |
| 2016/0296325 A1 | 10/2016 | Edelman et al. |
| 2016/0361167 A1 | 12/2016 | Tuval et al. |
| 2016/0361184 A1 | 12/2016 | Tabor et al. |
| 2017/0035435 A1 | 2/2017 | Amin et al. |
| 2017/0113026 A1 | 4/2017 | Finch |
| 2017/0128705 A1 | 5/2017 | Forcucci et al. |
| 2017/0135685 A9 | 5/2017 | McNamara et al. |
| 2017/0165532 A1 | 6/2017 | Khan et al. |
| 2017/0216025 A1 | 8/2017 | Nitzan et al. |

(56) References Cited

U.S. PATENT DOCUMENTS

| | | | |
|---|---|---|---|
| 2017/0224323 A1 | 8/2017 | Rowe et al. | |
| 2017/0224444 A1 | 8/2017 | Viecilli et al. | |
| 2017/0231766 A1 | 8/2017 | Hariton et al. | |
| 2017/0273790 A1 | 9/2017 | Vettukattil et al. | |
| 2017/0281339 A1 | 10/2017 | Levi et al. | |
| 2017/0312486 A1 | 11/2017 | Nitzan et al. | |
| 2017/0319823 A1 | 11/2017 | Yacoby et al. | |
| 2017/0325956 A1 | 11/2017 | Rottenberg et al. | |
| 2017/0348100 A1 | 12/2017 | Lane et al. | |
| 2018/0099128 A9 | 4/2018 | McNamara et al. | |
| 2018/0104053 A1 | 4/2018 | Alkhatib et al. | |
| 2018/0125630 A1 | 5/2018 | Hynes et al. | |
| 2018/0130988 A1 | 5/2018 | Nishikawa et al. | |
| 2018/0243071 A1 | 8/2018 | Eigerl et al. | |
| 2018/0256865 A1 | 9/2018 | Finch et al. | |
| 2018/0263766 A1 | 9/2018 | Nitzan et al. | |
| 2018/0280667 A1 | 10/2018 | Keren | |
| 2018/0344994 A1 | 12/2018 | Karavany et al. | |
| 2019/0000327 A1 | 1/2019 | Doan et al. | |
| 2019/0008628 A1 | 1/2019 | Eigler et al. | |
| 2019/0015188 A1 | 1/2019 | Eigler et al. | |
| 2019/0021861 A1 | 1/2019 | Finch | |
| 2019/0239754 A1 | 8/2019 | Nabutovsky et al. | |
| 2019/0262118 A1 | 8/2019 | Eigler et al. | |
| 2019/0328513 A1 | 10/2019 | Levi et al. | |
| 2019/0336163 A1 | 11/2019 | McNamara et al. | |
| 2020/0060825 A1 | 2/2020 | Rottenberg et al. | |
| 2020/0078558 A1 | 3/2020 | Yacoby et al. | |
| 2020/0085600 A1 | 3/2020 | Schwartz et al. | |

FOREIGN PATENT DOCUMENTS

| | | | |
|---|---|---|---|
| EP | 1965842 B1 | 11/2011 | |
| EP | 3400907 A1 | 11/2018 | |
| FR | 2827153 A1 | 1/2003 | |
| WO | WO-9727898 A1 | 8/1997 | |
| WO | WO-99/60941 A1 | 12/1999 | |
| WO | WO-00/44311 A2 | 8/2000 | |
| WO | WO-0110314 A2 | 2/2001 | |
| WO | WO-0226281 A1 | 4/2002 | |
| WO | WO-02/071974 A2 | 9/2002 | |
| WO | WO-03/053495 A2 | 7/2003 | |
| WO | WO-2005/027752 A1 | 3/2005 | |
| WO | WO-2005/074367 A1 | 8/2005 | |
| WO | WO-2006/127765 A1 | 11/2006 | |
| WO | WO-2007/083288 A2 | 7/2007 | |
| WO | WO-2008/055301 A1 | 5/2008 | |
| WO | WO-2009/029261 A1 | 3/2009 | |
| WO | WO-2010/128501 A1 | 11/2010 | |
| WO | WO-2010129089 A2 | 11/2010 | |
| WO | WO-2011062858 A1 | 5/2011 | |
| WO | WO-2013/096965 A1 | 6/2013 | |
| WO | WO-2016/178171 A1 | 11/2016 | |
| WO | WO-2017118920 A1 | 7/2017 | |
| WO | WO-2018158747 A1 | 9/2018 | |
| WO | WO-2019015617 A1 | 1/2019 | |
| WO | WO-2019085841 A1 | 5/2019 | |
| WO | WO-2019019013 A1 | 6/2019 | |
| WO | WO-2019142152 A1 | 7/2019 | |
| WO | WO-2019179447 A1 | 9/2019 | |
| WO | WO-2019218072 A1 | 11/2019 | |

OTHER PUBLICATIONS

Atrium Advanta V12, Balloon Expandable Covered Stent, Improving Patient Outcomes with an Endovascular Approach, Brochure—8 pages, Getinge (2017).

Braunwald, Heart Disease, Chapter 6, p. 186.

Bridges, et al., The Society of Thoracic Surgeons Practice Guideline Series: Transmyocardial Laser Revascularization, Ann Thorac Surg., 77:1494-1502 (2004).

Bristow et al., Improvement in cardiac myocite function by biological effects of medical therapy: a new concept in the treatment of heart failure, European Heart Journal 16 (Suppl.F): 20-31 (1995).

Case et al., "Relief of High Left-Atrial Pressure in Left-Ventricular Failure," Lancet, pp. 841-842 (Oct. 14, 1964).

Coats et al., "Controlled trial of physical training in chronic heart failure: Exercise performance, hemodynamics, ventilation and autonomic function," Circulation 85:2119-2131 (1992).

Partial International Search dated Aug. 17, 2017 in Int'l PCT Patent Appl. Serial No. PCT/IB2017/053188.

Davies et al., "Reduced contraction and altered frequency response of isolated ventricular myocytes from patients with heart failure," Circulation 92: 2540-2549 (1995).

Ennezat et al., An unusual case of low-flow, low-gradient severe aortic stenosis: Left-to-right shunt due to atrial septal defect, Cardiology 113(2): 146-148 (2009).

Ewert et al., "Acute left heart failure after interventional occlusion of an atrial septal defect," Z Kardiol. 90(5): 362-366 (May 2001).

Ewert et al., Masked Left Ventricular Restriction in Elderly Patients With Atrial Septal Defects: A Contraindication for Closure?, Catheterization and Cardiovascular Interventions 52: 177-180 (2001).

Extended EP Search Report dated Sep. 19, 2016 in EP Patent Application Serial No. 16170281.6.

Extended European Search Report dated Jan. 8, 2015 in EP Patent Appl No. 10772089.8.

Geiran et al., "Changes in cardiac dynamics by opening an interventricular shunt in dogs," J. Surg. Res. 48(1): 6-12 (Jan. 1990).

Gelernter-Yaniv et al., "Transcatheter closure of left-to-right interatrial shunts to resolve hypoxemia," Conginit. Heart Dis. 31(1) 47-53 (Jan. 2008).

Gewillig et al., "Creation with a stent of an unrestrictive lasting atrial communication," Cardio. Young 12(4): 404-407 (2002).

International Search Report & Written Opinion dated May 29, 2018 in Int'l PCT Patent Appl. Serial No. PCTIB2018/051355.

International Search Report for PCT/IL2005/000131, 3 pages (dated Apr. 7, 2008).

International Search Report for PCT/IL2010/000354 dated Aug. 25, 2010 (1 pg).

Int'l Search Report & Written Opinion dated Feb. 16, 2015 in Int'l PCT Patent Appl. Serial No. PCT/IB2014/001771.

Khositseth et al., Transcatheter Amplatzer Device Closure of Atrial Septal Defect and Patent Foramen Ovale in Patients With Presumed Paradoxical Embolism, Mayo Clinic Proc., 79:35-41 (2004).

Kramer et al., "Controlled study of captopril in chronic heart failure: A rest and exercise hemodynamic study," Circulation 67(4): 807-816 (1983).

Lai et al., Bidirectional Shunt Through a Residual Atrial Septal Defect After Percutaneous Transvenous Mitral Commissurotomy, Cardiology 83(3): 205-207 (1993).

Lemmer et al., "Surgical implications of atrial septal defect complicating aortic balloon valvuloplasty," Ann Thorac. Surg. 48(2): 295-297 (Aug. 1989).

Merriam-Webster "Definition of 'Chamber'," O-line Dictionary 2004, Abstract.

Park, et al., Blade Atrial Septostomy: Collaborative Study, Circulation, 66(2):258-266 (1982).

Roven et al., "Effect of Compromising Right Ventricular Function in Left Ventricular Failure by Means of Interatrial and Other Shunts," American Journal Cardiology, 24:209-219 (1969).

Salehian et al., Improvements in Cardiac Form and Function After Transcatheter Closure of Secundum Atrial Septal Defects, Journal of the American College of Cardiology, 45(4):499-504 (2005).

Schmitto et al., Chronic heart failure induced by multiple sequential coronary microembolization in sheep, The International Journal of Artificial Organs, 31(4):348-353 (2008).

Schubert et al., Left Ventricular Conditioning in the Elderly Patient to Prevent Congestive Heart Failure After Transcatheter Closure of the Atrial Septal Defect, Catheterization and Cardiovascular Interventions,64(3): 333-337 (2005).

Stormer et al., Comparative Study of n vitro Flow Characteristics Between a Human Aortic Valve and a Designed Aortic Valve and Six Corresponding Types of Prosthetic Heart Valves, European Surgical Research 8(2): 117-131 (1976).

Stumper et al., "Modified technique of stent fenestration of the atrial septum," Heart 89: 1227-1230 (2003).

(56) References Cited

OTHER PUBLICATIONS

Trainor et al., Comparative Pathology of an Implantable Left Atrial Pressure Sensor, ASAIO Journal, Clinical Cardiovascular/Cardiopulmonary Bypass, 59(5):486-92 (2013).
Zhou et al., Unidirectional Valve Patch for Repair of Cardiac Septal Defects With Pulmonary Hypertension, Annals of Thoracic Surgeons, 60:1245-1249 (1995).
International Search Report & Written Opinion dated Jul. 14, 2020 in Int'l PCT Patent Appl. Serial No. PCT/IB2020/053832.
International Search Report & Written Opinion dated Aug. 12, 2020 in Int'l PCT Patent Appl. Serial No. PCT/IB2020/053118.
Abraham et al., "Hemodynamic Monitoring in Advanced Heart Failure: Results from the LAPTOP-HF Trial," J Card Failure, 22:940 (2016) (Abstract Only).
Abraham et al., "Sustained efficacy of pulmonary artery pressure to guide adjustment of chronic heart failure therapy: complete follow-up results from the CHAMPION randomised trial," The Lancet, http://dx.doi.org/10.1016/S0140-6736(15)00723-0 (2015).
Abraham et al., "Wireless pulmonary artery haemodynamic monitoring in chronic heart failure: a randomised controlled trial," The Lancet, DOI:10.1016/S0140-6736(11)60101-3 (2011).
Abreu et al., "Doppler ultrasonography of the femoropopliteal segment in patients with venous ulcer," J Vasc Bras., 11(4):277-285 (2012).
Adamson et al., "Ongoing Right Ventricular Hemodynamics in Heart Failure Clinical Value of Measurements Derived From an Implantable Monitoring System," J Am Coll Cardiol., 41(4):565-571 (2003).
Adamson et al., "Wireless Pulmonary Artery Pressure Monitoring Guides Management to Reduce Decompensation in Heart Failure With Preserved Ejection Fraction," Circ Heart Fail., 7:935-944 (2014).
Ambrosy et al. "The Global Health and Economic Burden of Hospitalizations for Heart Failure," J Am Coll Cardiol., 63:1123-1133 (2014).
Aminde et al., "Current diagnostic and treatment strategies for Lutembacher syndrome: the pivotal role of echocardiography," Cardiovasc Diagn Ther., 5(2):122-132 (2015).
Anderas E. "Advanced MEMS Pressure Sensors Operating in Fluids," Digital Comprehensive Summaries of Uppsala Dissertation from the Faculty of Science and Technology 933. Uppsala ISBN 978-91-554-8369-2 (2012).
Anderas et al., "Tilted c-axis Thin-Film Bulk Wave Resonant Pressure Sensors with Improved Sensitivity," IEEE Sensors J., 12(8):2653-2654 (2012).
Ando et al., "Left ventricular decompression through a patent foramen ovale in a patient with hypertrophic cardiomyopathy: a case report," Cardiovascular Ultrasound 2(2):1-7 (2004).
Article 34 Amendments dated May 28, 2013 in related International PCT Patent Appl No. PCT/IB2012/001859.
Article 34 Amendments dated Nov. 27, 2012, as filed in related Int'l PCT Application No. PCT/IL2011/000958.
Ataya et al., "A Review of Targeted Pulmonary Arterial Hypertension-Specific Pharmacotherapy," J. Clin. Med., 5(12):114(2016).
Bannan et al., "Characteristics of Adult Patients with Atrial Septal Defects Presenting with Paradoxical Embolism.," Catheterization and Cardiovascular Interventions, 74:1066-1069 (2009).
Baumgartner et al., "ESC Guidelines for the management of grown-up congenital heart disease (new version 2010)—The Task Force on the Management of Grown-up Congenital Heart Disease of the European Society of Cardiology (ESC)," Eur Heart J., 31:2915-2957 (2010).
Beemath et al., "Pulmonary Embolism as a Cause of Death in Adults Who Died With Heart Failure," Am J Cardiol., 98:1073-1075 (2006).
Benza et al., "Monitoring Pulmonary Arterial Hypertension Using an Implantable Hemodynamic Sensor," CHEST, 156(6):1176-1186 (2019).
Boehm, et al., "Balloon Atrial Septostomy: History and Technique," Images Paeditr. Cardiol., 8(1):8-14(2006).
Bruch et al., "Fenestrated Occluders for Treatment of ASD in Elderly Patients with Pulmonary Hypertension and/or Right Heart Failure," J Interven Cardiol., 21(1):44-49 (2008).
Burkhoff et al., "Assessment of systolic and diastolic ventricular properties via pressure-volume analysis: a guide for clinical, translational, and basic researchers," Am J Physiol Heart Circ Physiol., 289:H501-H512 (2005).
Butler et al. "Recognizing Worsening Chronic Heart Failure as an Entity and an End Point in Clinical Trials," JAMA., 312(8):789-790 (2014).
Chakko et al., "Clinical, radiographic, and hemodynamic correlations in chronic congestive heart failure: conflicting results may lead to inappropriate care," Am J Medicine, 90:353-359 (1991) (Abstract Only).
Chang et al., "State-of-the-art and recent developments in micro/nanoscale pressure sensors for smart wearable devices and health monitoring systems," Nanotechnology and Precision Engineering, 3:43-52 (2020).
Chen et al., "Continuous wireless pressure monitoring and mapping with ultra-small passive sensors for health monitoring and critical care," Nature Communications, 5(1):1-10 (2014).
Chen et al., "National and Regional Trends in Heart Failure Hospitalization and Mortality Rates for Medicare Beneficiaries, 1998-2008," JAMA, 306(15):1669-1678 (2011).
Chiche et al., "Prevalence of patent foramen ovale and stroke in pulmonary embolism patients," Eur Heart J., 34:P1142 (2013) (Abstract Only).
Chin et al., "The right ventricle in pulmonary hypertension," Coron Artery Dis., 16(1):13-18 (2005) (Abstract Only).
Chun et al., "Lifetime Analysis of Hospitalizations and Survival of Patients Newly Admitted With Heart Failure," Circ Heart Fail., 5:414-421 (2012).
Ciarka et al., "Atrial Septostomy Decreases Sympathetic Overactivity in Pulmonary Arterial Hypertension," Chest, 131(6):P1831-1837 (2007) (Abstract Only).
Cleland et al., "The EuroHeart Failure survey programme—a survey on the quality of care among patients with heart failure in Europe—Part 1: patient characteristics and diagnosis," Eur Heart J., 24:442-463 (2003).
Clowes et al., "Mechanisms of Arterial Graft Healing—Rapid Transmural Capillary Ingrowth Provides a Source of Intimal Endothelium and Smooth Muscle in Porous PTFE Prostheses," Am J Pathol., 123:220-230 (1986).
Davies et al., "Abnormal left heart function after operation for atrial septal defect," British Heart Journal, 32:747-753 (1970).
Del Trigo et al., "Unidirectional Left-To-Right Interatrial Shunting for Treatment of Patients with Heart Failure with Reduced Ejection Fraction: a Safety and Proof-of-Principle Cohort Study," Lancet, 387:1290-1297 (2016).
Della Lucia et al., "Design, fabrication and characterization of SAW pressure sensors for offshore oil and gas exploration," Sensors and Actuators A: Physical, 222:322-328 (2015).
Drazner et al., "Prognostic Importance of Elevated Jugular Venous Pressure and a Third Heart Sound in Patients with Heart Failure," N Engl. J Med., 345(8):574-81 (2001).
Drazner et al., "Relationship between Right and Left-Sided Filling Pressures in 1000 Patients with Advanced Heart Failure," Heart Lung Transplant, 18:1126-1132 (1999).
Drexel, et al., "The Effects of Cold Work and Heat Treatment on the Properties of Nitinol Wire, Proceedings of the International Conference on Shape Memory and Superelastic Technologies, SMST 2006," Pacific Grove, California, USA (pp. 447-454) May 7-11, 2006.
Eigler et al., "Cardiac Unloading with an Implantable Interatrial Shunt in Heart Failure: Serial Observations in an Ovine Model of Ischemic Cardiomyopathy," Structural Heart, 1:40-48 (2017).
Eigler, et al., Implantation and Recovery of Temporary Metallic Stents in Canine Coronary Arteries, JACC, 22(4):1207-1213 (1993).
Eshaghian et al., "Relation of Loop Diuretic Dose to Mortality in Advanced Heart Failure," Am J Cardiol., 97:1759-1764 (2006).
Ewert, et al., Masked Left Ventricular Restriction in Elderly Patients With Atrial Septal Defects: A Contraindication for Closure?, Catheterization and Cardiovascular Intervention, 52:177-180 (2001).

(56) References Cited

OTHER PUBLICATIONS

Extended European Search Report dated Mar. 29, 2019 in EP Patent Appl. Serial No. EP16789391.
Feldman et al., "Transcatheter Interatrial Shunt Device for the Treatment of Heart Failure with Preserved Ejection Fraction (Reduce LAP-HF I [Reduce Elevated Left Atrial Pressure in Patients With Heart Failure]), A Phase 2, Randomized, Sham-Controlled Trial," Circulation, 137:364-375 (2018).
Ferrari et al., "Impact of pulmonary arterial hypertension (PAH) on the lives of patients and carers: results from an international survey," Eur Respir J., 42:26312 (2013) (Abstract Only).
Fonarow et al., "Characteristics, Treatments, and Outcomes of Patients With Preserved Systolic Function Hospitalized for Heart Failure," J Am Coll Cardiol., 50(8):768-777 (2007).
Fonarow et al., "Risk Stratification for In-Hospital Mortality in Acutely Decompensated Heart Failure: Classification and Regression Tree Analysis," JAMA, 293(5):572-580 (2005).
Fonarow, G., "The Treatment Targets in Acute Decompensated Heart Failure," Rev Cardiovasc. Med., 2:(2):S7-S12 (2001).
Galie et al., "2015 ESC/ERS Guidelines for the diagnosis and treatment of pulmonary hypertension—The Joint Task Force for the Diagnosis and Treatment of Pulmonary Hypertension of the European Society of Cardiology (ESC) and the European Respiratory Society (ERS)," European Heart Journal, 37:67-119 (2016).
Galie et al., "Pulmonary arterial hypertension: from the kingdom of the near-dead to multiple clinical trial meta-analyses," Eur Heart J., 31:2080-2086 (2010).
Galipeau et al., "Surface acoustic wave microsensors and applications," Smart Materials and Structures, 6(6):658-667 (1997) (Abstract Only).
Geva et al., "Atrial septal defects," Lancet, 383:1921-32 (2014).
Gheorghiade et al., "Acute Heart Failure Syndromes, Current State and Framework for Future Research," Circulation, 112:3958-3968 (2005).
Gheorghiade et al., "Effects of Tolvaptan, a Vasopressin Antagonist, in Patients Hospitalized With Worsening Heart Failure A Randomized Controlled Trial," JAMA., 291:1963-1971 (2004).
Go et al. "Heart Disease and Stroke Statistics—2014 Update—A Report From the American Heart Association," Circulation, 128:1-267 (2014).
Guillevin et al., "Understanding the impact of pulmonary arterial hypertension on patients' and carers' lives," Eur Respir Rev., 22:535-542 (2013).
Guyton et al., "Effect of Elevated Left Atrial Pressure and Decreased Plasma Protein Concentration on the Development of Pulmonary Edema," Circulation Research, 7:643-657 (1959).
Hasenfub et al., "A transcatheter intracardiac shunt device for heart failure with preserved ejection fraction (Reduce LAP-HF): a multicentre, open-label, single-arm, phase 1 trial," Lancet, 387:1298-304 (2016).
Hasenfub, et al., A Transcatheter Intracardiac Shunt Device for Heart Failure with Preserved Ejection Fraction (Reduce LAP-HF): A Multicentre, Open-Label, Single-Arm, Phase 1 Trial, www.thelancet.com, 387:1298-1304 (2016).
Hoeper et al., "Definitions and Diagnosis of Pulmonary Hypertension," J Am Coll Cardiol., 62(5):D42-D50 (2013).
Hogg et al., "Heart Failure With Preserved Left Ventricular Systolic Function. Epidemiology, Clinical Characteristics, and Prognosis," J Am Coll Cardiol., 43(3):317-327 (2004).
Howell et al., "Congestive heart failure and outpatient risk of venous thromboembolism: A retrospective, case-control study," Journal of Clinical Epidemiology, 54:810-816 (2001).
Huang et al., "Remodeling of the chronic severely failing ischemic sheep heart after coronary microembolization: functional, energetic, structural, and cellular responses," Am J Physiol Heart Circ Physiol., 286:H2141-H2150 (2004).
Humbert et al., "Pulmonary Arterial Hypertension in France—Results from a National Registry," Am J Respir Crit Care Med., 173:1023-1030 (2006).
International Search Report & Written Opinion dated Nov. 7, 2016 in Int'l PCT Patent Appl. Serial No. PCT/IB2016/052561.

International Search Report & Written Opinion dated May 29, 2018 in Int'l PCT Patent Appl. Serial No. PCT/IB2018/051385.
International Search Report & Written Opinion dated Feb. 6, 2013 in Int'l PCT Patent Appl. No. PCT/IB2012/001859, 12 pages.
International Search Report & Written Opinion dated Feb. 7, 2020 in Int'l PCT Patent Appl. Serial No. PCT/IB2019/060257.
International Search Report & Written Opinion dated Mar. 19, 2015 in Int'l PCT Patent Appl. Serial No. PCT/IB2014/002920.
International Search Report & Written Opinion dated May 13, 2019 in Int'l PCT Patent Appl. No. PCT/IB2019/050452.
International Search Report & Written Opinion dated Jul. 20, 2020 in Int'l PCT Patent Appl. Serial No. PCT/IB2020/054699.
International Search Report & Written Opinion dated Aug. 28, 2012 in Int'l PCT Patent Appl. No. PCT/IL2011/000958.
International Search Report & Written Opinion dated Sep. 21, 2020 in Int'l PCT Patent Appl. Serial No. PCT/IB2020/054306.
International Search Report & Written Opinion dated Oct. 26, 2007 in Int'l PCT Patent Appl. Serial No. PCT/IB07/50234.
Jessup et al. "2009Focused Update: ACC/AHA Guidelines for the Diagnosisand Management of Heart Failure in Adults: A Report of the American College ofCardiology Foundation/American Heart Association Task Force on PracticeGuidelines: Developed in Collaboration With the International Society for Heartand Lung Transplantation," J. Am. Coll. Cardiol., 53:1343-1382 (2009).
Jiang, G., "Design challenges of implantable pressure monitoring system," Frontiers in Neuroscience, 4(29):1-4 (2010).
Kane et al., "Integration of clinical and hemodynamic parameters in the prediction of long-term survival in patients with pulmonary arterial hypertension," Chest, 139(6):1285-1293 (2011) (Abstract Only).
Kaye et al., "Effects of an Interatrial Shunt on Rest and Exercise Hemodynamics: Results of a Computer Simulation in Heart Failure," Journal of Cardiac Failure, 20(3): 212-221 (2014).
Kaye et al., "One-Year Outcomes After Transcatheter Insertion of an Interatrial Shunt Device for the Management of Heart Failure With Preserved Ejection Fraction," Circulation: Heart Failure, 9(12):e003662 (2016).
Keogh et al., "Interventional and Surgical Modalitiesof Treatment in Pulmonary Hypertension," J Am Coll Cardiol., 54:S67-77 (2009).
Kretschmar et al., "Shunt Reduction With a Fenestrated Amplatzer Device," Catheterization and Cardiovascular Interventions, 76:564-571 (2010).
Kropelnicki et al., "CMOS-compatible ruggedized high-temperature Lamb wave pressure sensor," J. Micromech. Microeng., 23:085018 pp. 1-9 (2013).
Krumholz et al., "Patterns of Hospital Performance in Acute Myocardial Infarction and Heart Failure 30-Day Mortality and Readmission," Circ Cardiovasc Qual Outcomes, 2:407-413 (2009).
Kulkarni et al., "Lutembacher's syndrome," J Cardiovasc Did Res., 3(2):179-181 (2012).
Kurzyna et al., "Atrial Septostomy in Treatment of End-Stage Right Heart Failure in Patients With Pulmonary Hypertension," Chest, 131:977-983 (2007).
Lammers et al., "Efficacy and Long-Term Patency of Fenerstrated Amplatzer Devices in Children," Catheter Cardiovasc Interv., 70:578-584 (2007).
Lindenfeld et al. "Executive Summary: HFSA 2010 Comprehensive Heart Failure Practice Guideline," J. Cardiac Failure, 16(6):475-539 (2010).
Luo, Yi,Selective and Regulated RF Heating of Stent Toward Endohyperthermia Treatment of In-Stent Restenosis, a Thesis Submitted in Partial Fulfillment of the Requirements for the Degree of Master of Applied Science in the Faculty of Graduate and Postdoctoral Studies (Electrical and Computer Engineering), The University of British Columbia, Vancouver, Dec. 2014.
MacDonald et al., "Emboli Enter Penetrating Arteries of Monkey Brain in Relation to Their Size," Stroke, 26:1247-1251 (1995).
Maluli et al., "Atrial Septostomy: A Contemporary Review," Clin. Cardiol., 38(6):395-400 (2015).
Maurer et al., "Rationale and Design of the Left Atrial Pressure Monitoring to Optimize Heart Failure Therapy Study (LAPTOP-HF)," J Cardiac Fail., 21:479-488 (2015).

(56) References Cited

OTHER PUBLICATIONS

McClean et al., "Noninvasive Calibration of Cardiac Pressure Transducers in Patients With Heart Failure: An Aid to Implantable Hemodynamic Monitoring and Therapeutic Guidance," J Cardiac Failure, 12(7):568-576 (2006).
McLaughlin et al., "Management of Pulmonary Arterial Hypertension," J Am Coll Cardiol., 65(18):1976-1997 (2015).
McLaughlin et al., "Survival in Primary Pulmonary Hypertension—The Impact of Epoprostenol Therapy.," Circulation, 106:1477-1482 (2002).
Mu et al., "Dual mode acoustic wave sensor for precise pressure reading," Applied Physics Letters, 105:113507-1-113507-5 (2014).
Nagaragu et al., "A 400 µW Differential FBAR Sensor Interface IC with digital readout," IEEE., pp. 218-221 (2015).
Noordegraaf et al., "The role of the right ventricle in pulmonary arterial hypertension," Eur Respir Rev., 20(122):243-253 (2011).
O'Byrne et al., "The effect of atrial septostomy on the concentration of brain-type natriuretic peptide in patients with idiopathic pulmonary arterial hypertension," Cardiology in the Young, 17(5):557-559 (2007) (Abstract Only).
Oktay et al., "The Emerging Epidemic of Heart Failure with Preserved Ejection Fraction," Curr Heart Fail Rep., 10(4):1-17 (2013).
Owan et al., "Trends in Prevalence and Outcome of Heart Failure with Preserved Ejection Fraction," N Engl J Med., 355:251-259 (2006).
Paitazoglou et al., "Title: The AFR-PRELIEVE Trial: A prospective, non-randomized, pilot study to assess the Atrial Flow Regulator (AFR) in Heart Failure Patients with either preserved or reduced ejection fraction," EuroIntervention, 28:2539-50 (2019).
Park Blade Septostomy Catheter Instructions for Use, Cook Medical, 28 pages, Oct. 2015.
Partial Supplemental European Search Report dated Dec. 11, 2018 in EP Patent Appl. Serial No. 16789391.6.
Peters et al., "Self-fabricated fenestrated Amplatzer occluders for transcatheter closure of atrial septal defect in patients with left ventricular restriction: midterm results," Clin Res Cardiol., 95:88-92 (2006).
Ponikowski et al., "2016 ESC Guidelines for the diagnosis and treatment of acute and chronic heart failure. The Task Force for the diagnosis and treatment of acute and chronic heart failure of the European Society of Cardiology (ESC)," Eur Heart J., doi:10.1093/eurheartj/ehw128 (2016).
Potkay, J. A., "Long term, implantable blood pressure monitoring systems," Biomed Microdevices, 10:379-392 (2008).
Pretorious et al., "An Implantable Left Atrial Pressure Sensor Lead Designed for Percutaneous Extraction Using Standard Techniques," PACE, 00:1-8 (2013).
Rajeshkumar et al., "Atrial septostomy with a predefined diameter using a novel occlutech atrial flow regulator improves symptoms and cardiac index in patients with severe pulmonary arterial hypertension," Catheter Cardiovasc Interv., 1-9 (2017).
Rich et al., "Atrial Septostomy as Palliative Therapy for Refractory Primary Pulmonary Hypertension," Am J Cardiol., 51:1560-1561 (1983).
Ritzema et al., "Direct Left Atrial Pressure Monitoring in Ambulatory Heart Failure Patients—Initial Experience With a New Permanent Implantable Device," Circulation, 116:2952-2959 (2007).
Ritzema et al., "Physician-Directed Patient Self-Management of Left Atrial Pressure in Advanced Chronic Heart Failure," Circulation, 121:1086-1095 (2010).
Roberts et al., "Integrated microscopy techniques for comprehensive pathology evaluation of an implantable left atrial pressure sensor," J Histotechnology, 36(1):17-24 (2013).
Rodes-Cabau et al., "Interatrial Shunting for Heart Failure Early and Late Results From the First-in-Human Experience With the V-Wave System," J Am Coll Cardiol Intv., 11:2300-2310.doi:10.1016/j.cin.2018.07.001 (2018).
Rosenquist et al., Atrial Septal Thickness and Area in Normal Heart Specimens and in Those With Ostium Secundum Atrial Septal Defects, J. Clin. Ultrasound, 7:345-348 (1979).
Ross et al., "Interatrial Communication and Left Atrial Hypertension—A Cause of Continuous Murmur," Circulation, 28:853-860 (1963).
Rossignol, et al., Left-to-Right Atrial Shunting: New Hope for Heart Failure, www.thelancet.com, 387:1253-1255 (2016).
Sandoval et al., "Effect of atrial septostomy on the survival of patients with severe pulmonary arterial hypertension," Eur Respir J., 38:1343-1348 (2011).
Sandoval et al., "Graded Balloon Dilation Atrial Septostomy in Severe Primary Pulmonary Hypertension—A Therapeutic Alternative for Patients Nonresponsive to Vasodilator Treatment," JACC, 32(2):297-304 (1998).
Schiff et al., "Decompensated heart failure: symptoms, patterns of onset, and contributing factors," Am J. Med., 114(8):625-630 (2003) (Abstract Only).
Schneider et al., "Fate of a Modified Fenestration of Atrial Septal Occluder Device after Transcatheter Closure of Atrial Septal Defects in Elderly Patients," J Interven Cardiol., 24:485-490 (2011).
Scholl et al., "Surface Acoustic Wave Devices for Sensor Applications," Phys Status Solidi Appl Res., 185(1):47-58 (2001) (Abstract Only).
Schubert et al., "Left Ventricular Conditioning in the Elderly Patient to Prevent Congestive Heart Failure After Transcatheter Closure of Atrial Septal Defect," Cardiovasc Interv., 64:333-337 (2005).
Setoguchi et al., "Repeated hospitalizations predict mortality in the community population with heart failure," Am Heart J., 154:260-266 (2007).
Shah et al., "Heart Failure With Preserved, Borderline, and Reduced Ejection Fraction—5-Year Outcomes," J Am Coll Cardiol., https://doi.org/10.1016/j.jacc.2017.08.074 (2017).
Shah et al., "One-Year Safety and Clinical Outcomes of a Transcatheter Interatrial Shunt Device for the Treatment of Heart Failure With Preserved Ejection Fraction in the Reduce Elevated Left Atrial Pressure in Patients With Heart Failure (Reduce LAP-HF I) Trial—A Randomized Clinical Trial," JAMA Cardiol. doi:10.1001/jamacardio.2018.2936 (2018).
Sitbon et al., "Selexipag for the Treatment of Pulmonary Arterial Hypertension.," N Engl J Med., 373(26):2522-2533 (2015).
Sitbon et al., "Epoprostenol and pulmonary arterial hypertension: 20 years of clinical experience," Eur Respir Rev., 26:160055:1-14 (2017).
Steimle et al., "Sustained Hemodynamic Efficacy of Therapy Tailored to Reduce Filling Pressures in Survivors With Advanced Heart Failure," Circulation, 96:1165-1172 (1997).
Stevenson et al., "The Limited Reliability of Physical Signs for Estimating Hemodynamics in Chronic Heart Failure," JAMA, 261(6):884-888 (1989) (Abstract Only).
Su et al., "A film bulk acoustic resonator pressure sensor based on lateral field excitation," International Journal of DistributedSensor Networks, 14(11):1-8 (2018).
Supplementary European Search Report dated Nov. 13, 2009 in EP Patent Appl. Serial No. 05703174.2.
Thenappan et al., "Evolving Epidemiology of Pulmonary Arterial Hypertension," Am J Resp Critical Care Med., 186:707-709 (2012).
Tomai et al., "Acute Left Ventricular Failure After Transcatheter Closure of a Secundum Atrial Septal Defect in a Patient With Coronary Artery Disease: A Critical Reappraisal," Catheterization and Cardiovascular Interventions, 55:97-99 (2002).
Torbicki et al., "Atrial Septostomy," The Right Heart, 305-316 (2014).
Trainor et al., "Comparative Pathology of an Implantable Left Atrial Pressure Sensor," ASAIO Journal, 59:486-492 (2013).
Troost et al., "A Modified Technique of Stent Fenestration of the Interatrial Septum Improves Patients With Pulmonary Hypertension," Catheterization and Cardiovascular Interventions, 73:173179 (2009).
Troughton et al., "Direct Left Atrial Pressure Monitoring in Severe Heart Failure: Long-Term Sensor Performance," J. of Cardiovasc. Trans. Res., 4:3-13 (2011).

(56) References Cited

OTHER PUBLICATIONS

Vank-Noordegraaf et al., "Right Heart Adaptation to Pulmonary Arterial Hypertension—Physiology and Pathobiology," J Am Coll Cardiol., 62(25):D22-33 (2013).
Verel et al., "Comparison of left atrial pressure and wedge pulmonary capillary pressure—Pressure gradients between left atrium and left ventricle," British Heart J., 32:99-102 (1970).
Viaene et al., "Pulmonary oedema after percutaneous ASD-closure," Acta Cardiol., 65(2):257-260 (2010).
Wang et al., "A Low Temperature Drifting Acoustic Wave Pressure Sensor with an Integrated Vacuum Cavity for Absolute Pressure Sensing," Sensors, 20(1788):1-13 (2020).
Warnes et al., "ACC/AHA 2008 Guidelines for the Management of Adults With Congenital Heart Disease—A Report of the American College of Cardiology/American Heart Association Task Force on Practice Guidelines (Writing Committee to Develop Guidelines on the Management of Adults With Congenital Heart Disease)," JACC, 52(23):e143-e263 (2008).
Webb et al., "Atrial Septal Defects in the Adult Recent Progress and Overview," Circulation, 114:1645-1653 (2006).
Wiedemann, H.R., "Earliest description by Johann Friedrich Meckel, Senior (1750) of what is known today as Lutembacher syndrome (1916)," Am J Med Genet., 53(1):59-64 (1994) (Abstract Only).
Yantchev et al., "Thin Film Lamb Wave Resonators in Frequency Control and Sensing Applications: A Review," Journal of Micromechanics and Microengineering, 23(4):043001 (2013).
Zhang et al., "Acute left ventricular failure after transcatheter closure of a secundum atrial septal defect in a patient with hypertrophic cardiomyopathy," Chin Med J., 124(4):618-621 (2011).
Zhang et al., "Film bulk acoustic resonator-based high-performance pressure sensor integrated with temperature control system," J Micromech Microeng., 27(4):1-10 (2017).

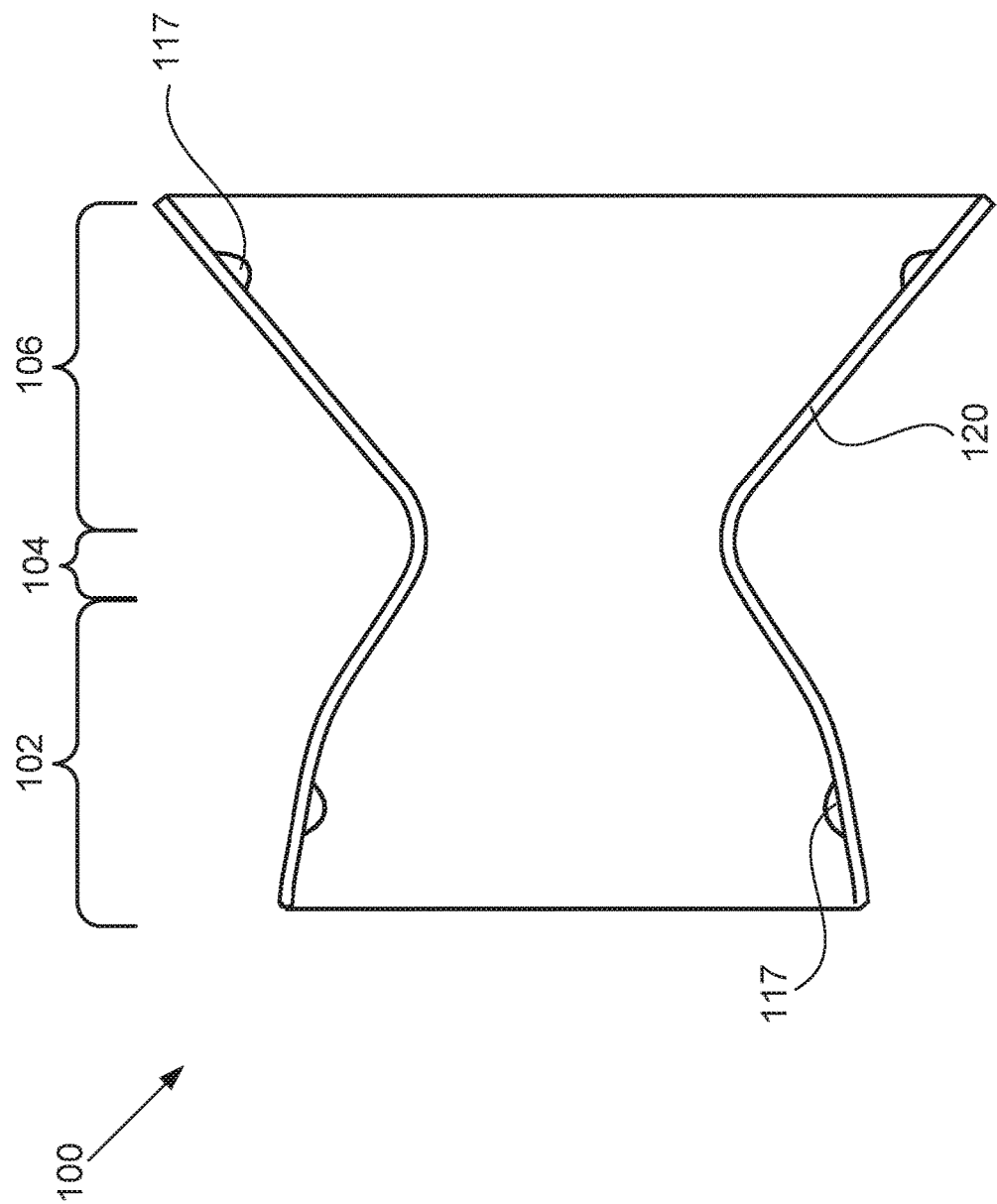

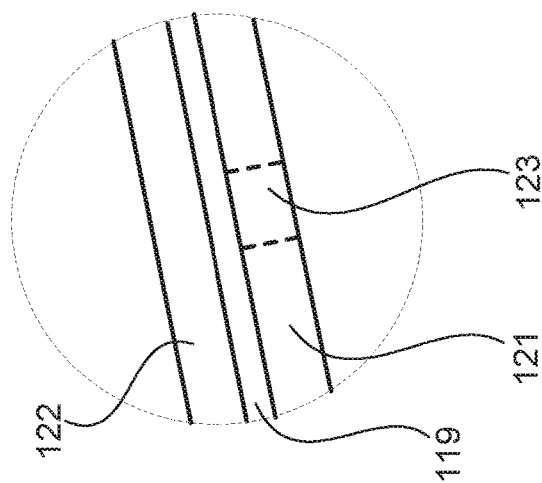
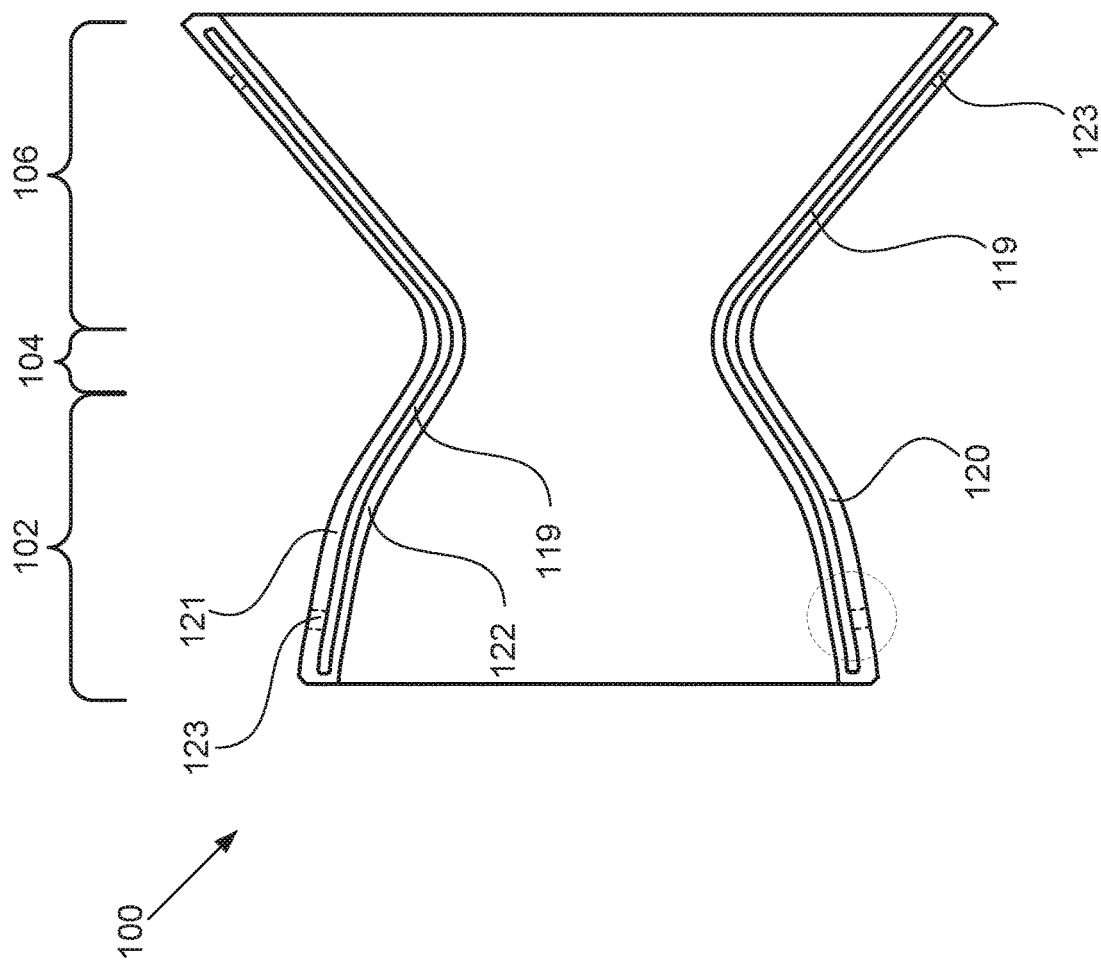
FIG. 1F
FIG. 1E

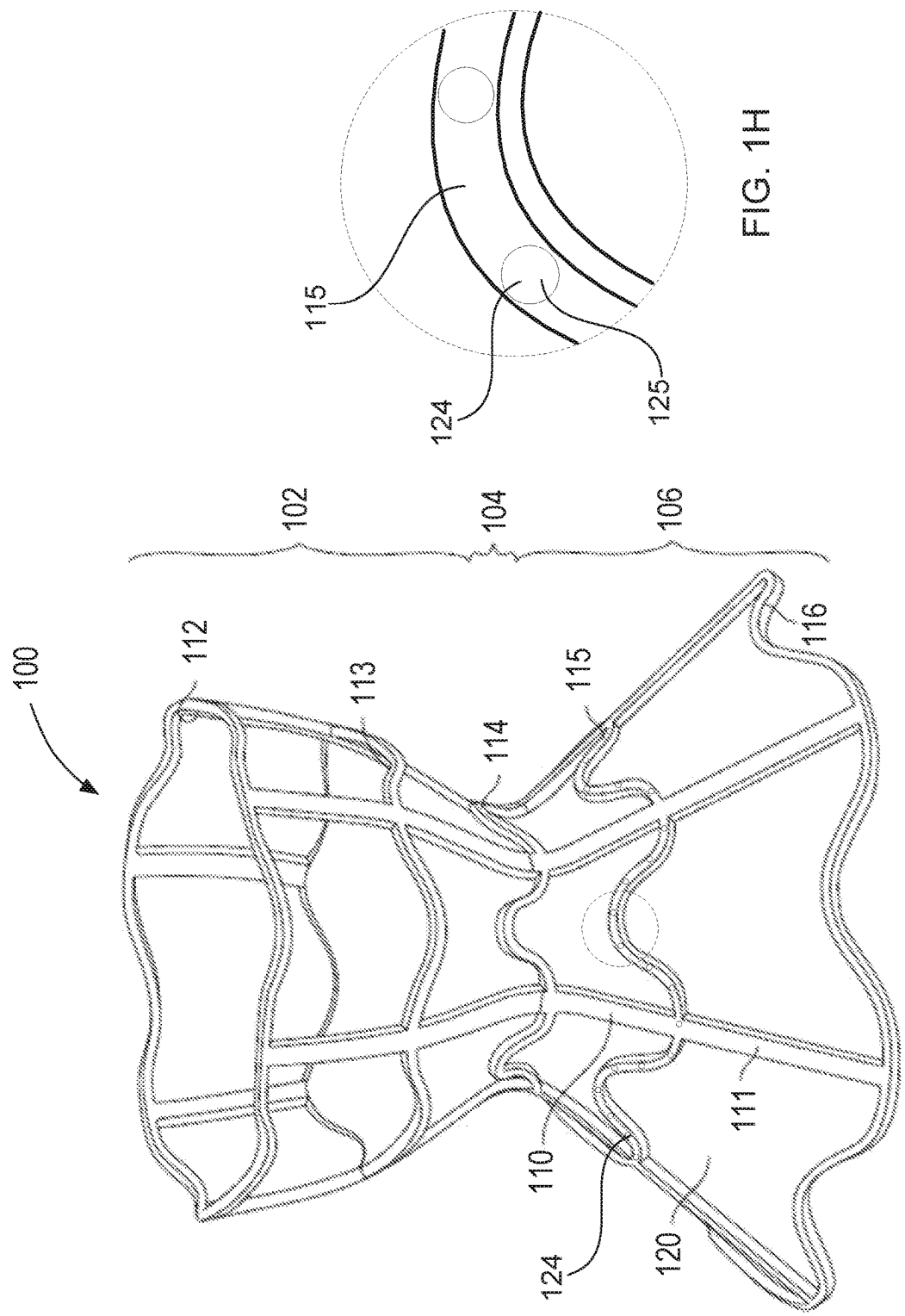

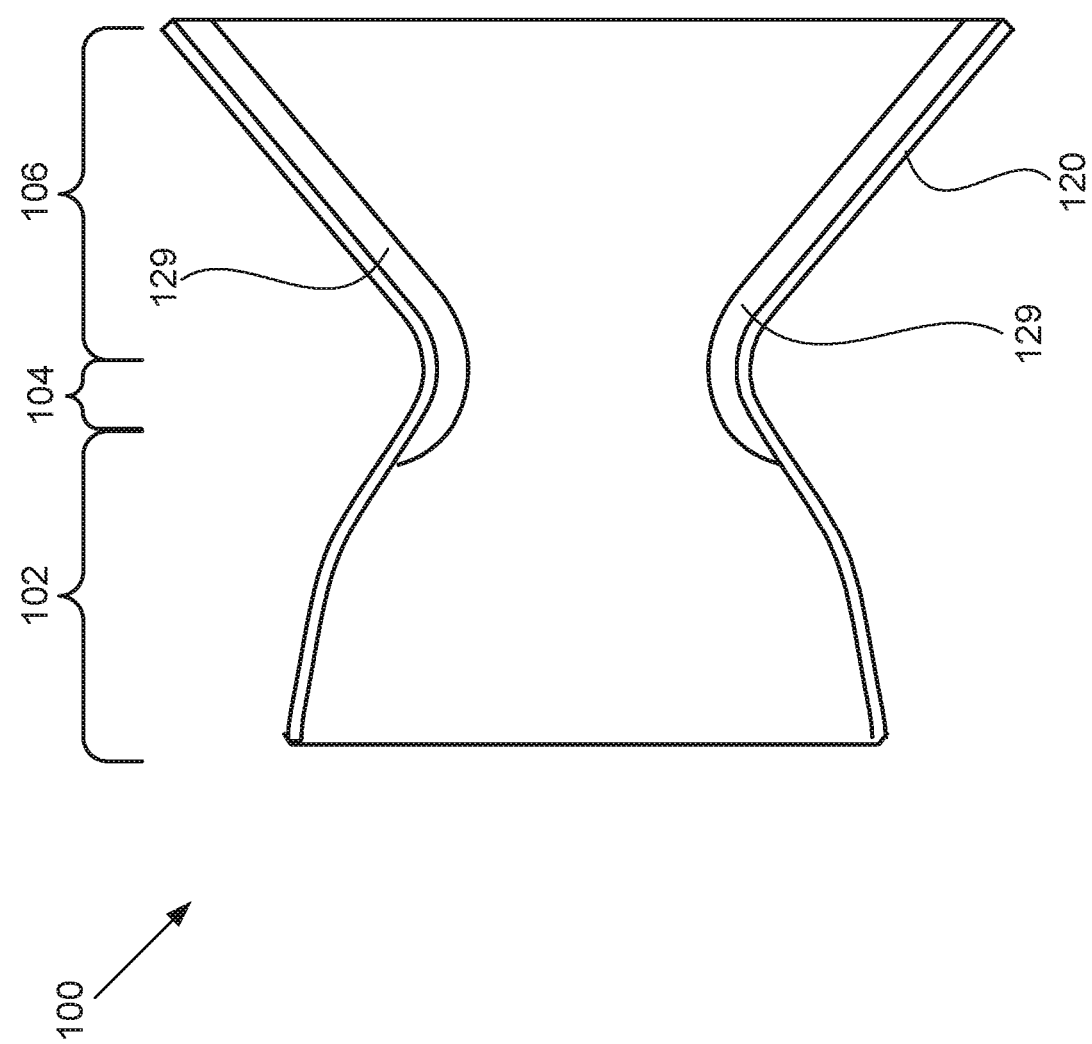

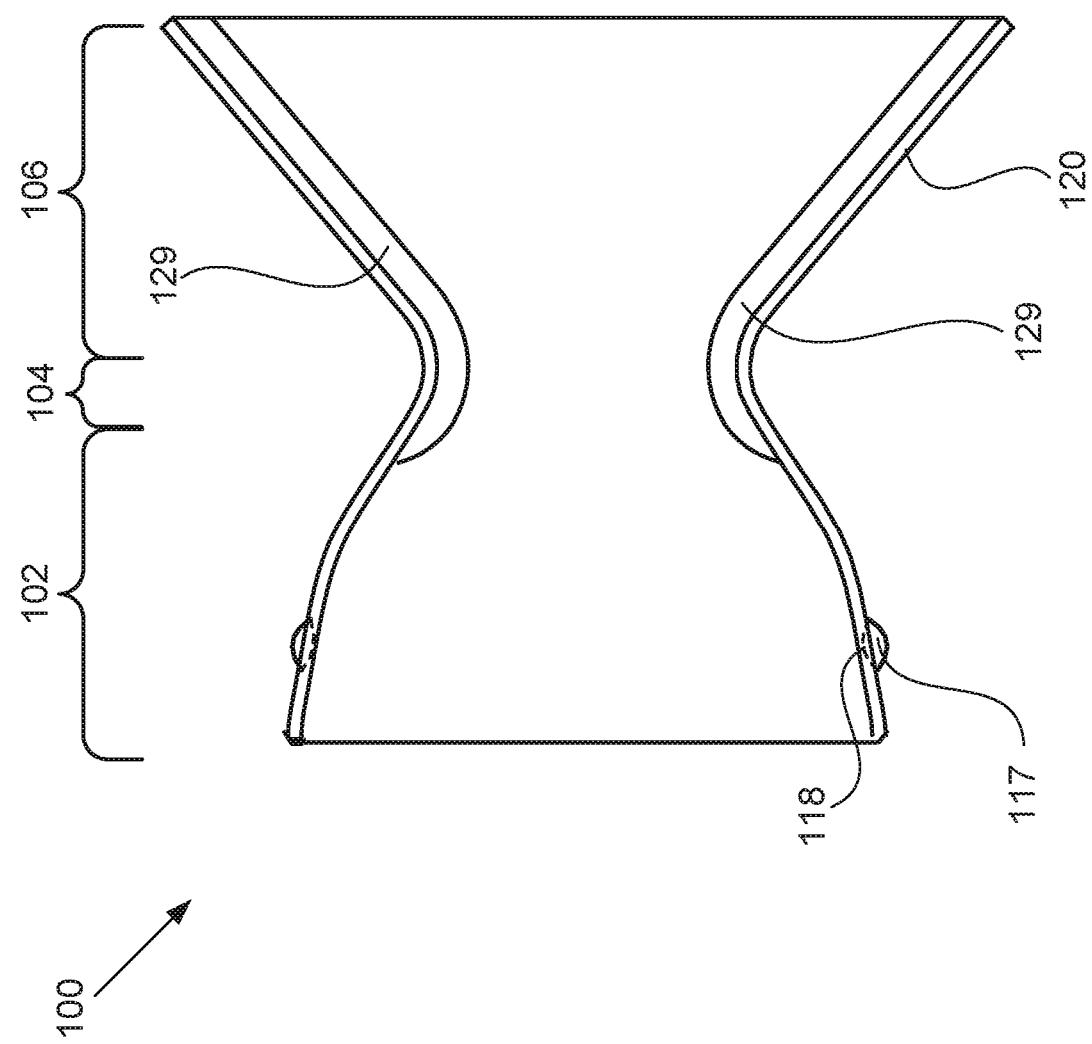

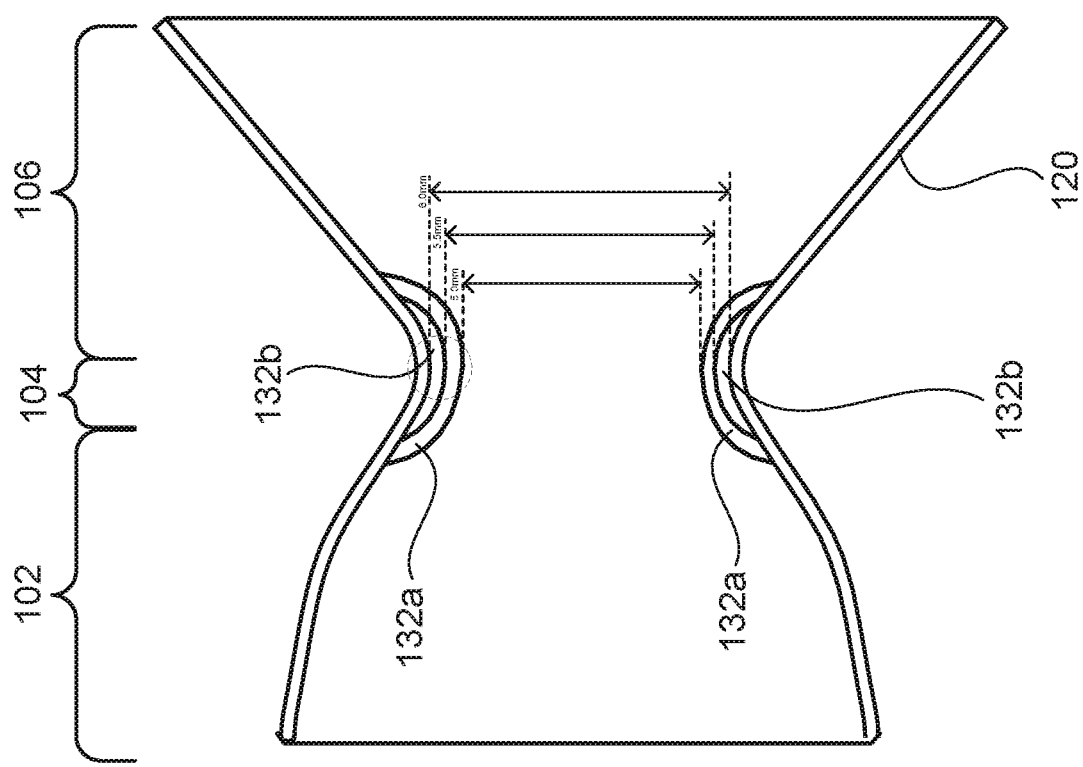
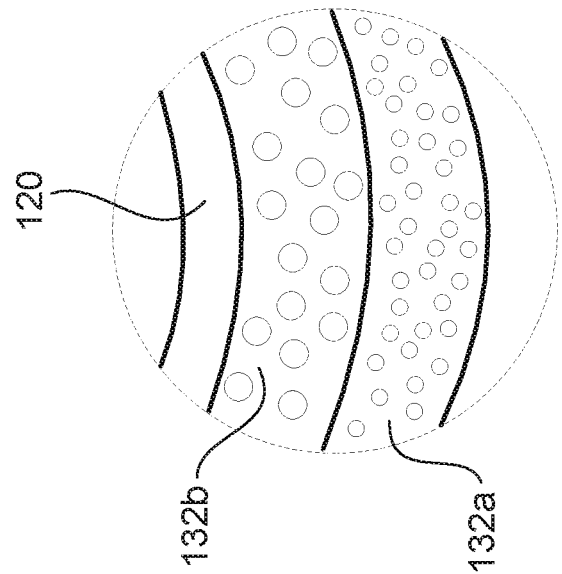
FIG. 7A
FIG. 7B

INTERATRIAL SHUNTS HAVING BIODEGRADABLE MATERIAL, AND METHODS OF MAKING AND USING SAME

CROSS-REFERENCE TO RELATED APPLICATION

This application is a continuation-in-part of U.S. patent application Ser. No. 15/492,852, filed Apr. 20, 2017, which is a continuation of U.S. patent application Ser. No. 13/193,309, filed Jul. 28, 2011, now U.S. Pat. No. 9,629,715, the entire contents of each of which are incorporated herein by reference.

FIELD OF THE INVENTION

This application generally relates to devices and methods for reducing left atrial pressure, particularly in subjects with heart pathologies such as congestive heart failure (CHF), pulmonary hypertension, or myocardial infarction (MI), using an interatrial shunt that may include a drug eluting material that reduces neoplasia.

BACKGROUND

The human heart is comprised of four major chambers with two ventricles and two atria. Generally, the right-side heart receives oxygen-poor blood from the body into the right atrium and pumps it via the right ventricle to the lungs. The left-side heart receives oxygen-rich blood from the lungs into the left atrium and pumps it via the left ventricle to the aorta for distribution throughout the body. Due to any of a number of illnesses, including coronary artery disease, high blood pressure (hypertension), valvular regurgitation and calcification, damage to the heart muscle as a result of infarction or ischemia, myocarditis, congenital heart defects, abnormal heart rhythms or various infectious diseases, the left ventricle may be rendered less effective and thus unable to pump oxygenated blood throughout the body.

Heart failure is the physiological state in which cardiac output is insufficient to meet the needs of the body and the lungs. CHF occurs when cardiac output is relatively low and the body becomes congested with fluid. There are many possible underlying causes of CHF, including myocardial infarction, coronary artery disease, valvular disease, and myocarditis. Chronic heart failure is associated with neurohormonal activation and alterations in autonomic control. Although these compensatory neurohormonal mechanisms provide valuable support for the heart under normal physiological circumstances, they also have a fundamental role in the development and subsequent progression of CHF. For example, one of the body's main compensatory mechanisms for reduced blood flow in CHF is to increase the amount of salt and water retained by the kidneys. Retaining salt and water, instead of excreting it into the urine, increases the volume of blood in the bloodstream and helps to maintain blood pressure. However, the larger volume of blood also stretches the heart muscle, enlarging the heart chambers, particularly the ventricles. At a certain amount of stretching, the heart's contractions become weakened, and the heart failure worsens. Another compensatory mechanism is vasoconstriction of the arterial system. This mechanism, like salt and water retention, raises the blood pressure to help maintain adequate perfusion.

In low ejection fraction (EF) heart failure, high pressures in the heart result from the body's attempt to maintain the high pressures needed for adequate peripheral perfusion. However, the heart weakens as a result of the high pressures, aggravating the disorder. Pressure in the left atrium may exceed 25 mmHg, at which stage, fluids from the blood flowing through the pulmonary circulatory system flow out of the interstitial spaces and into the alveoli, causing pulmonary edema and lung congestion.

Table 1 lists typical ranges of right atrial pressure (RAP), right ventricular pressure (RVP), left atrial pressure (LAP), left ventricular pressure (LVP), cardiac output (CO), and stroke volume (SV) for a normal heart and for a heart suffering from CHF. In a normal heart beating at around 70 beats/minute, the stroke volume needed to maintain normal cardiac output is about 60 to 100 milliliters. When the preload, after-load, and contractility of the heart are normal, the pressures required to achieve normal cardiac output are listed in Table 1. In a heart suffering from CHF, the hemodynamic parameters change (as shown in Table 1) to maximize peripheral perfusion.

TABLE 1

| Parameter | Normal Range | CHF Range |
| --- | --- | --- |
| RAP (mmHg) | 2-6 | 6-15 |
| RVP (mmHg) | 15-25 | 20-40 |
| LAP (mmHg) | 6-12 | 15-30 |
| LVP (mmHg) | 6-120 | 20-220 |
| CO (liters/minute) | 4-8 | 2-6 |
| SV (milliliters/beat) | 60-100 | 30-80 |

CHF is generally classified as either systolic heart failure (SHF) or diastolic heart failure (DHF). In SHF, the pumping action of the heart is reduced or weakened. A common clinical measurement is the ejection fraction, which is a function of the blood ejected out of the left ventricle (stroke volume), divided by the maximum volume remaining in the left ventricle at the end of diastole or relaxation phase. A normal ejection fraction is greater than 50%. Systolic heart failure has a decreased ejection fraction of less than 50%. A patient with SHF may usually have a larger left ventricle because of a phenomenon called cardiac remodeling that occurs secondarily to the higher ventricular pressures.

In DHF, the heart generally contracts normally, with a normal ejection fraction, but is stiffer, or less compliant, than a healthy heart would be when relaxing and filling with blood. This stiffness may impede blood from filling the heart, and produce backup into the lungs, which may result in pulmonary venous hypertension and lung edema. DHF is more common in patients older than 75 years, especially in women with high blood pressure.

Both variants of CHF have been treated using pharmacological approaches, which typically involve the use of vasodilators for reducing the workload of the heart by reducing systemic vascular resistance, as well as diuretics, which inhibit fluid accumulation and edema formation, and reduce cardiac filling pressure.

In more severe cases of CHF, assist devices such as mechanical pumps have been used to reduce the load on the heart by performing all or part of the pumping function normally done by the heart. Chronic left ventricular assist devices (LVAD), and cardiac transplantation, often are used as measures of last resort. However, such assist devices are typically intended to improve the pumping capacity of the heart, to increase cardiac output to levels compatible with normal life, and to sustain the patient until a donor heart for transplantation becomes available. Such mechanical devices enable propulsion of significant volumes of blood (liters/min), but are limited by a need for a power supply, relatively large pumps, and the risk of hemolysis, thrombus formation, and infection. Temporary assist devices, intra-aortic balloons, and pacing devices have also been used.

In addition to cardiac transplant, which is highly invasive and limited by the ability of donor hearts, surgical approaches such as dynamic cardiomyoplastic or the Batista partial left ventriculectomy may also be used in severe cases.

Various devices have been developed using stents or conduits to modify blood pressure and flow within a given vessel, or between chambers of the heart. For example, U.S. Pat. No. 6,120,534 to Ruiz is directed to an endoluminal stent for regulating the flow of fluids through a body vessel or organ, for example for regulating blood flow through the pulmonary artery to treat congenital heart defects. The stent may include an expandable mesh having lobed or conical portions joined by a constricted region, which limits flow through the stent. The mesh may comprise longitudinal struts connected by transverse sinusoidal or serpentine connecting members. Ruiz is silent on the treatment of CHF or the reduction of left atrial pressure.

U.S. Pat. No. 6,468,303 to Amplatz et al. discloses a collapsible medical device and associated method for shunting selected organs and vessels. Amplatz discloses that the device may be suitable to shunt a septal defect of a patient's heart, for example, by creating a shunt in the atrial septum of a neonate with hypoplastic left heart syndrome (HLHS). Amplatz discloses that increasing mixing of pulmonary and systemic venous blood improves oxygen saturation. Amplatz discloses that depending on the hemodynamics, the shunting passage can later be closed by an occluding device. Amplatz is silent on the treatment of CHF or the reduction of left atrial pressure, as well as on means for regulating the rate of blood flow through the device.

U.S. Patent Publication No. 2005/0165344 to Dobak, III discloses an apparatus for treating heart failure that includes a conduit positioned in a hole in the atrial septum of the heart, to allow flow from the left atrium into the right atrium. Dobak discloses that the shunting of blood will reduce left atrial pressures, thereby preventing pulmonary edema and progressive left ventricular dysfunction, and reducing LVEDP. Dobak discloses that the conduit may include a self-expandable tube with retention struts, such as metallic arms that exert a slight force on the atrial septum on both sides and pinch or clamp the valve to the septum, and a one-way valve member, such as a tilting disk, bileaflet design, or a flap valve formed of fixed animal pericardial tissue. However, Dobak states that a valved design may not be optimal due to a risk of blood stasis and thrombus formation on the valve, and that valves can also damage blood components due to turbulent flow effects. Dobak does not provide any specific guidance on how to avoid such problems.

A significant drawback of previous devices is the susceptibility to narrow or close during the post-implantation healing period. For example, neoendocardial tissue overgrowth, referred to as pannus, grows from the underlining tissue to cover the mesh and narrow or partially occlude the shunt orifice. During the period following implantation, local trauma caused by crossing and dilating the FO, plus the chronic effects of continuous pressure applied by the mesh material on the septal tissue, provoke a localized healing response. This response entails activation of an inflammatory process, attracting lymphocytes and macrophages to the area of tissue injury. These inflammatory cells in turn release a variety of cytokines that signal fibroblasts and smooth-muscle cells from the wound margins to dedifferentiate, migrate, proliferate and encapsulate affected portions of the implanted device. The fibroblasts and smooth muscle cells then secrete extracellular matrix material composed of collagen and proteoglycans, which extracellular matrix forms the bulk of the pannus. The duration of this healing phase in humans is typically up to 6-9 months, but may be longer if there is a chronic source for tissue injury such as device compression or erosion of adjacent tissue. Eventually this pannus is covered with neoendothelial cells, causing the pannus growth to stop or stabilize. In the long term, the collagen of the pannus remodels, but generally retains its space occupying properties. Such tissue overgrowth typically spreads over the surfaces of the implant's struts, and may substantially narrow the orifice lumen or even entirely occlude the shunt. Narrowing or occlusion of the shunt prevents LA decompression and limits any positive effect for the patient.

Thus, there exists a need for a more durable shunt configuration that reduces tissue overgrowth and maintains luminal patency for extended periods of time.

SUMMARY OF THE INVENTION

Embodiments of the present invention provide hourglass-shaped devices for reducing left atrial pressure having a drug-eluting material that reduces neoplasia, and methods of making and using the same. As elaborated further herein, such reductions in left atrial pressure may increase cardiac output, relieve pulmonary congestion, and lower pulmonary artery pressure, among other benefits. The inventive devices are configured for implantation through the atrial septum, and particularly through the middle of the fossa ovalis, away from the surrounding limbus, inferior vena cava (IVC), and atrial wall. The devices are configured to provide blood flow between the left atrium and the right atrium, e.g., when the pressure in the left atrium exceeds the pressure in the right atrium, and thus decompress the left atrium. The devices may include a biodegradable material that gradually biodegrades over time to increase the cross-sectional flow area of the device, so as to offset a flow rate decrease caused by tissue overgrowth and thus maintain a suitable flow rate over time.

As described in greater detail below, lowering the left atrial pressure using the inventive devices may offset abnormal hemodynamics associated with CHF, for example, to reduce congestion as well as the occurrence of acute cardiogenic pulmonary edema (ACPE), which is a severe manifestation of CHF in which fluid leaks from pulmonary capillaries into the interstitium and alveoli of the lung. In particular, lowering the left atrial pressure may improve the cardiac function by:

(1) Decreasing the overall pulmonary circulation pressure, thus decreasing the afterload on the heart, (2) Increasing cardiac output by reducing left ventricular end systolic dimensions, and (3) Reducing the left ventricular end-diastolic pressure (LVEDP) and pulmonary artery pressure (PAP), which in turn may enable the heart to work more efficiently and over time increase cardiac output. For example, the oxygen uptake of the myocardium may be reduced, creating a more efficient working point for the myocardium.

In accordance with one aspect of the present invention, inventive devices for regulating blood pressure between a patient's left atrium and right atrium to treat a cardiovascular condition, e.g., pulmonary hypertension, heart failure, or myocardial infarction, include a stent having a first flared end region, a second flared end region, a neck region disposed between the first and second flared end regions, where the neck region is sized and shaped to engage a fossa ovalis of the patient's atrial septum. For example, the stent may be formed of a plurality of rings interconnected by a plurality of longitudinally extending struts. The stent has a passageway extending from an inlet of the first flared end region through the neck region and out an outlet of the second flared end region, such that blood is shunted between the left atrium and the right atrium through the passageway. The stent may transition between a collapsed state suitable for percutaneous delivery and an expanded state when deployed across the patient's fossa ovalis. For example, the stent has an hourglass configuration in the expanded state.

In addition, the stent has a biocompatible material disposed on the stent to define a continuous sheath that channels blood flow through the passageway. For example, the stent may be formed of a shape memory metal coated with the biocompatible material from the neck region to the second flared end region. In addition, the biocompatible material may be disposed in the neck region, the second flared end region, and a portion of the first flared end region of the stent. The biocompatible material may include ultra-high-molecular-weight-polyethylene (UHMWPE), expanded-polytetrafluoroethylene (ePTFE), polyurethane, DACRON (polyethylene terephthalate), silicone, polycarbonate urethane, or pericardial tissue from an equine, bovine, or porcine source, or any combination thereof. The biocompatible material disposed on the stent may inhibit excessive tissue overgrowth.

The stent further includes a biodegradable material disposed on the device adjacent to the inlet of the first flared end region and/or the outlet of the second flared end region, wherein the biodegradable material inhibits tissue overgrowth across the biodegradable material. The biodegradable material may include collagen-terpolymer, polylactic acid (PLA), poly L-lactic acid (PLLA), polyglycolic acid (PGA), poly(lactic-co-glycolic) acid copolymer (PLGA), poly(ε-caprolactone), methacrylated dextran-aminoethyl methacrylate copolymer (Dex-MA/AEMA), polydiaxanone, poly(glycerol sebacate) (PGS), polysialic acid (PSA), collagen type I/III, chitosan, or chitin, or any combination thereof.

In addition, the biodegradable material may include a drug, e.g., an "-olimus" drug such as sirolimus (rapamycin), deposited within the biodegradable material, wherein the drug inhibits tissue overgrowth such that the biodegradable material biodegrades after implantation to release the drug to inhibit tissue overgrowth across the biodegradable material. The biodegradable material may include a first biodegradable layer having a first concentration of the drug, and a second biodegradable layer having a second concentration of the drug different from the first concentration of the drug. The biodegradable material may be formed of a first biodegradable layer having a first biodegradable rate and a second biodegradable layer having a second biodegradable rate different from the first biodegradable rate.

In accordance with one aspect of the present invention, at least one of the plurality of rings of the stent includes one or more depressions formed on a surface of the ring(s). The biodegradable material may be disposed within the one or more depressions. The biocompatible material may include a first biocompatible material layer and a second biocompatible material layer, and the biodegradable material may be sandwiched between the first and second biocompatible material layers. The first and/or second biocompatible material layers may include a plurality of nodal pores sized and shaped to permit the drug to be released via the nodal pore(s) as the biodegradable material biodegrades.

The biodegradable material may include one or more biodegradable rings disposed on a surface of the biocompatible material adjacent to the inlet of the first flared end region and/or the outlet of the second flared end region. The one or more biodegradable rings inhibit tissue overgrowth across biodegradable ring(s). The biodegradable rings may be disposed on the biocompatible material on an inner surface of the stent and/or and outer surface of the stent. The biocompatible material may include one or more cavities extending through a surface of the biocompatible material, such that one or more biodegradable rings are disposed within the one or more cavities.

In accordance with another aspect of the present invention, the stent may have a biodegradable substance layer disposed on the biocompatible material at an inner surface of the neck region to define a cross-sectional area of a blood flow path, wherein the biodegradable substance layer biodegrades after implantation to increase the cross-sectional area of the blood flow path at the neck region over time. For example, the biodegradable substance layer may biodegrade after implantation to increase diameter of the blood flow path cross-sectional area at the neck region from an initial diameter of 5 mm to a diameter of 6 mm over at least a month. In accordance with another aspect of the claimed invention, the biodegradable substance layer biodegrades responsive to application of an external stimulus, e.g., heat or a biocompatible degradation activating material. In addition, the biodegradable substance layer may include a first biodegradable substance layer that biodegrades responsive to application of a first external stimulus, and a second biodegradable substance layer that biodegrades responsive to application of a second external stimulus different from the first external stimulus.

In accordance with yet another aspect of the present invention, a method of treating a subject with a cardiovascular condition, e.g., pulmonary hypertension, heart failure, or myocardial infarction, the subject having a heart with an atrial septum having a fossa ovalis therein, is provided. The method includes selecting a stent having a neck region between first and second flared end regions and a passageway extending from an inlet of the first flared end region through the neck region and out an outlet of the second flared end region, the stent further having a biocompatible material disposed on the stent and a biodegradable material disposed on the biocompatible material adjacent to at least the inlet of the first flared end region and the outlet of the second flared end region. The method further includes deploying the stent at a puncture through the fossa ovalis such that the neck region is positioned in the puncture, the first flared end region is disposed in the right atrium, and the second flared end region is disposed in the left atrium. The method also includes shunting blood between the left atrium and the right atrium through the passageway, wherein the biodegradable material inhibits tissue overgrowth across the biodegradable material.

The biodegradable material may include a drug, e.g., an "-olimus" drug, deposited within the biodegradable material, wherein the drug inhibits tissue overgrowth. Accordingly, the method further includes biodegrading the biodegradable material to release the drug such that tissue overgrowth is inhibited across the biodegradable material.

The stent may further include a biodegradable substance layer disposed on the biocompatible material at an inner surface of the neck region, such that the method further includes biodegrading the biodegradable substance layer after implantation to increase a cross-sectional area at the neck region.

BRIEF DESCRIPTION OF THE DRAWINGS

FIGS. 1B-1D illustrate the hourglass-shaped device of FIG. 1A having one or more drug-eluting biodegradable rings disposed thereon, according to some embodiments of the present invention.

FIGS. 1E-1F illustrate the hourglass-shaped device of FIG. 1A having a drug-eluting biodegradable material disposed within the biocompatible material of the device, according to some embodiments of the present invention.

FIGS. 1G-1H illustrate the hourglass-shaped device of FIG. 1A having a drug-eluting biodegradable material embedded within the stent of the device, according to some embodiments of the present invention.

FIG. 1K illustrates the hourglass-shaped device of FIG. 1A having a biodegradable substance layer disposed thereon, according to some embodiments of the present invention.

FIG. 1M illustrates the hourglass-shaped device of FIG. 1A having one or more drug-eluting biodegradable rings as well as a biodegradable substance layer disposed thereon, according to some embodiments of the present invention.

FIGS. 6A and 6B illustrate the hourglass-shaped device of FIG. 1A having a layer of degradable components disposed thereon, according to some embodiments of the present invention.

FIGS. 7A and 7B illustrate the hourglass-shaped device of FIG. 1A having multiple layers of degradable components disposed thereon, according to some embodiments of the present invention.

DETAILED DESCRIPTION

Figure 1A:
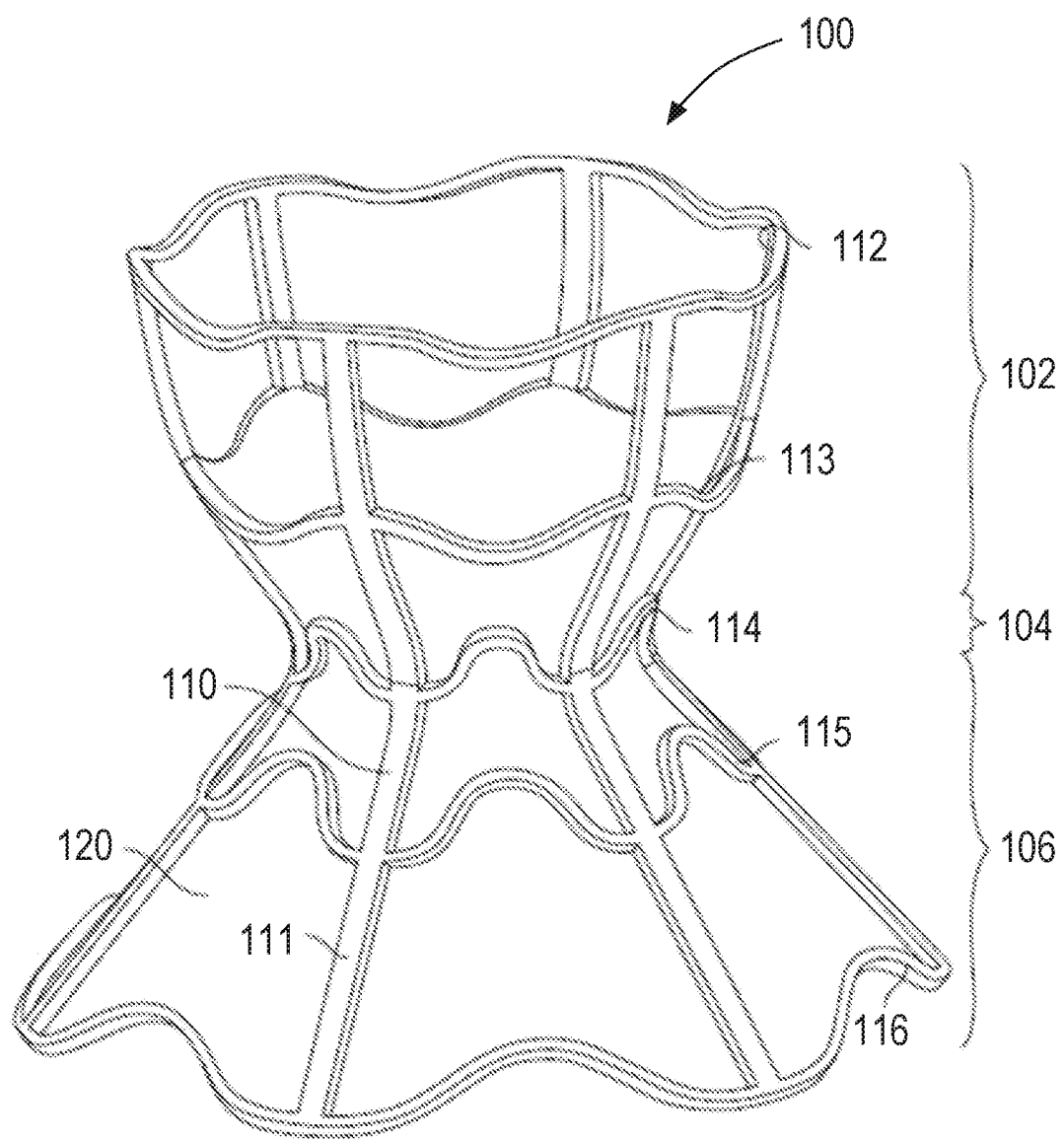
FIG. 1A illustrates an exemplary hourglass-shaped device, according to some embodiments of the present invention.

Embodiments of the present invention are directed to devices that reduce left atrial pressure, and thus may be useful in treating subjects suffering from congestive heart failure (CHF) or other disorders associated with elevated left atrial pressure. Specifically, the inventive device includes an hourglass or "diabolo" shaped stent, preferably formed of a shape memory metal. The stent is configured to lodge securely in the atrial septum, preferably in the fossa ovalis, and to allow blood to flow between the left atrium and the right atrium when blood pressure in the left atrium exceeds that on the right. Usefully, the inventive devices are configured so as to reduce blood pressure in the left atrium even when the pressure differential therebetween is relatively low; to provide a smooth flow path, thus inhibiting turbulence and high shear stresses that would otherwise promote thrombus formation; and to have a relatively small implantation footprint so as to inhibit tissue overgrowth and inflammatory response. Additionally, the inventive devices include a biodegradable material that releases a drug that reduces neoplasia so as to reduce tissue overgrowth and thus maintain a suitable flow rate through the device. The inventive devices also may include a biodegradable material that modifies the characteristics of blood flow through the device over time, specifically by increasing the cross-sectional area of the flow path so as to offset decreases in the flow path caused by tissue overgrowth. As such, the overall flow rate of the device may be maintained within a desired range over time, notwithstanding tissue overgrowth.

FIGS. 1A-1J illustrate various views of illustrative embodiments of the inventive device. First, with reference to FIG. 1A, device 100 includes an hourglass-shaped stent 110 and biocompatible material 120. Device 100 has three general regions: first flared or funnel-shaped end region 102, second flared or funnel-shaped end region 106, and neck region 104 disposed between the first and second flared end regions. Neck region 104 is configured to lodge in a puncture formed in the atrial septum, preferably in the fossa ovalis, using methods described in greater detail below. First flared end region 102 is configured to engage the right side of the atrial septum, and second flared end region 106 is configured to flank the left side of the atrial septum, when implanted. The particular dimensions and configurations of neck region 104 and first and second flared end regions 102, 106 may be selected so as to inhibit the formation of eddy currents when implanted, and thus inhibit thrombus formation; to inhibit tissue overgrowth in selected regions; to promote tissue overgrowth in other selected regions; and to provide a desirable rate of blood flow between the left and right atria. As discussed in greater detail below with respect to FIGS. 1B-1J, a biodegradable material may be disposed on the interior and/or exterior surface of the biocompatible material, within the biocompatible material, and/or embedded in the stent, such that the biodegradable material biodegrades to release a drug for inhibiting tissue overgrowth. In addition, as discussed in greater detail below with respect to FIG. 1L, a biodegradable substance layer may be disposed on the interior surfaces of second flared end region 106 and neck region 104 so as to dynamically modify the constriction of these components over time, to compensate for tissue overgrowth.

Hourglass-shaped stent 110 is preferably formed of a shape memory metal, e.g., NITINOL, or any other suitable material known in the art. Stent 110 includes a plurality of rings, e.g., sinusoidal rings 112-116, interconnected by longitudinally extending struts 111. Rings 112-116 and struts 111 may be of unitary construction, that is, entire stent 110 may be laser cut from a tube of shape memory metal. As can be seen in FIG. 1A, neck region 104 and second flared end region 106 are covered with biocompatible material 120, for example a sheet of a polymer such as expanded polytetrafluoroethylene (ePTFE), silicone, polycarbonate urethane, DACRON (polyethylene terephthalate), or polyurethane, or of a natural material such as pericardial tissue, e.g., from an equine, bovine, or porcine source. Specifically, the region extending approximately from sinusoidal ring 113 to sinusoidal ring 116 is covered with biocompatible material 120. Material 120 preferably is generally smooth so as to inhibit thrombus formation, and optionally may be impregnated with carbon so as to promote tissue ingrowth, i.e., ingrowth of tissue into the porous biocompatable fabric (neointima formation). Preferably, portions of stent 110 associated with first flared end region 102 are not covered with the biocompatible material, but are left as bare metal, so as to inhibit the formation of stagnant flow regions in the right atrium, so as to inhibit significant tissue overgrowth on device 100, i.e., undesireable overgrowth of pannus into the shunt lumen. The bare metal regions of stent 110, as well as any other regions of the stent, optionally may be electropolished or otherwise treated so as to inhibit thrombus formation, using any suitable method known in the art. As will be understood by a person having ordinary skill in the art, first flared end region 102 also may be covered with biocompatible material 120 such that the region extending approximately from sinusoidal ring 112 to sinusoidal ring 116 is covered with biocompatible material 120.

In accordance with one aspect of the present invention, hourglass-shaped stent 110 includes a biodegradable material disposed thereon adjacent to at least the outlet end or inlet end of hourglass-shaped device 100, which biodegrades over time to inhibit or reduce tissue overgrowth over the biodegradable material. The biodegradable material may comprise any suitable material that the body will gradually bioresorb or biodegrade, for example a hydrogel (e.g., polyethylene glycol hydrogel), synthetic polymer, or biological polymer. Examples of suitable synthetic polymers may include collagen-terpolymer; poly(lactic-co-glycolic) acids such as polylactic acid (PLA), poly L-lactic acid (PLLA), polyglycolic acid (PGA), and poly(lactic-co-glycolic) acid copolymer (PLGA); poly(ε-caprolactone); methacrylated dextran-aminoethyl methacrylate copolymer (Dex-MA/AEMA); polydiaxanone; and poly(glycerol sebacate) (PGS). Examples of suitable biological polymers may include polysialic acid (PSA), collagen type I/III, chitosan, and chitin. These materials are meant to be purely illustrative, and it should be appreciated that any suitable biodegradable or bioresorbable material may be used.

The biodegradable material is designed to bioresorb or biodegrade gradually over time to thereby inhibit tissue overgrowth. For example, the biodegradable material may have a drug, e.g., an -olimus drug, embedded therein that is released over time as the biodegradable material bioresorb or biodegrade. As the drug is released, tissue overgrowth is inhibited across the biodegradable material.

Figure 1B:
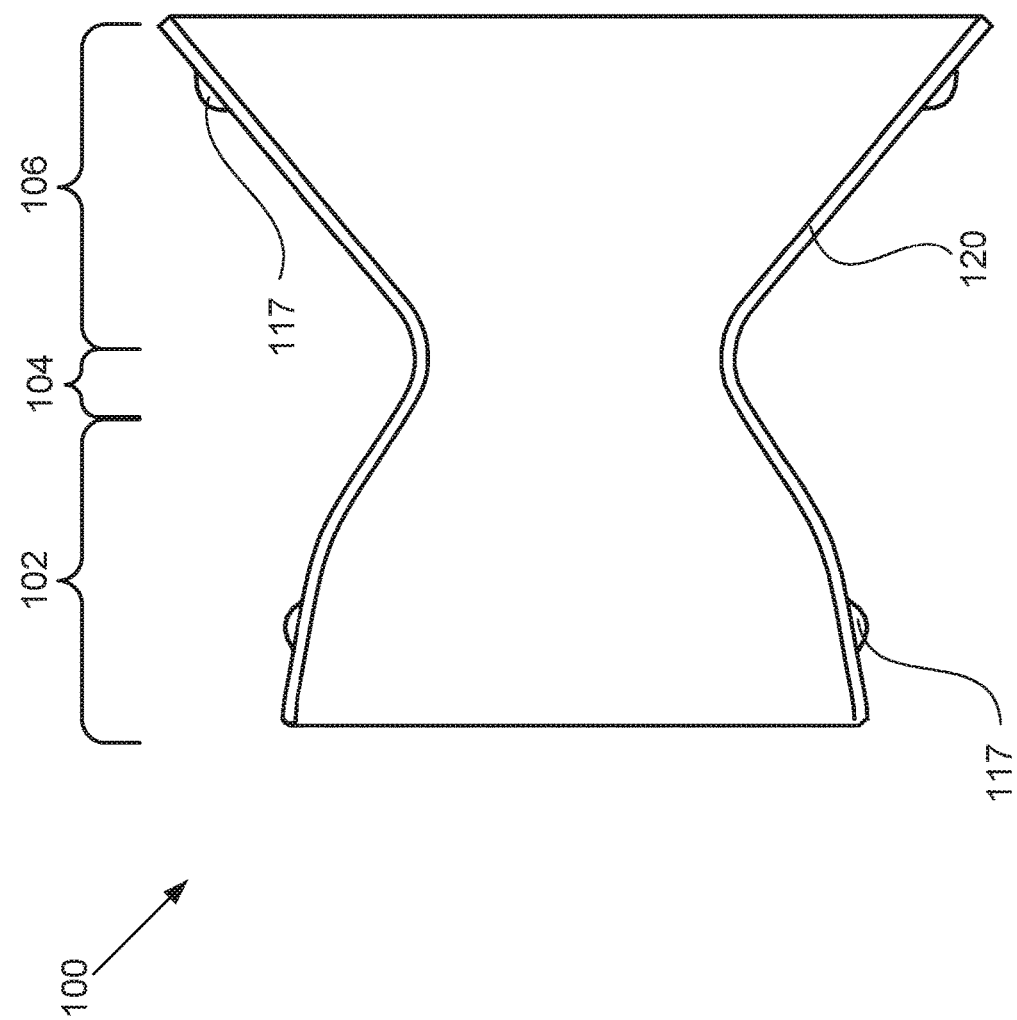

Referring now to FIGS. 1B and 1C, the biodegradable material of device 100 may be in the form of one or more biodegradable rings for inhibiting tissue overgrowth. Hourglass-shaped device 100 includes one or more biodegradable rings 117 disposed circumferentially along the surface of biocompatible material 120, preferably adjacent to at least the outlet end or inlet end of hourglass-shaped device 100. As biodegradable rings 117 bioresorb or biodegrade over time, the drug therein is released, which inhibits tissue overgrowth across the biodegradable rings. As such, one or more biodegradable rings 117 may be positioned adjacent to at least the inlet end of second flared end region 106 or outlet end of first flared end region 102 of device 100, and/or adjacent neck region 104 such that tissue overgrowth from the atrial septum is limited. Thus, the tissue overgrowth from the atrial septum may assist in anchoring device 100 to the atrial septum, while not excessively expanding so as to interfere with the patency of device 100.

FIG. 1B illustrates one or more biodegradable rings 117 disposed on the outer surface of biocompatible material 120, whereas FIG. 1C illustrates one or more biodegradable rings 117 disposed on the inner surface of biocompatible material 120. As will be understood by a person having ordinary skill in the art, any combination of one or more biodegradable rings 117 may be utilized to effectively reduce tissue overgrowth to preserve longevity and patency of device 100. As described above, alternatively or additionally, one or more biodegradable rings 117 may be disposed on the inner and/or outer surface of biocompatible material 120 adjacent neck region 104 of device 100. In addition, any of the shunts described above may utilize the biodegradable rings described herein for limiting tissue overgrowth across the biodegradable rings.

Figure 1D:
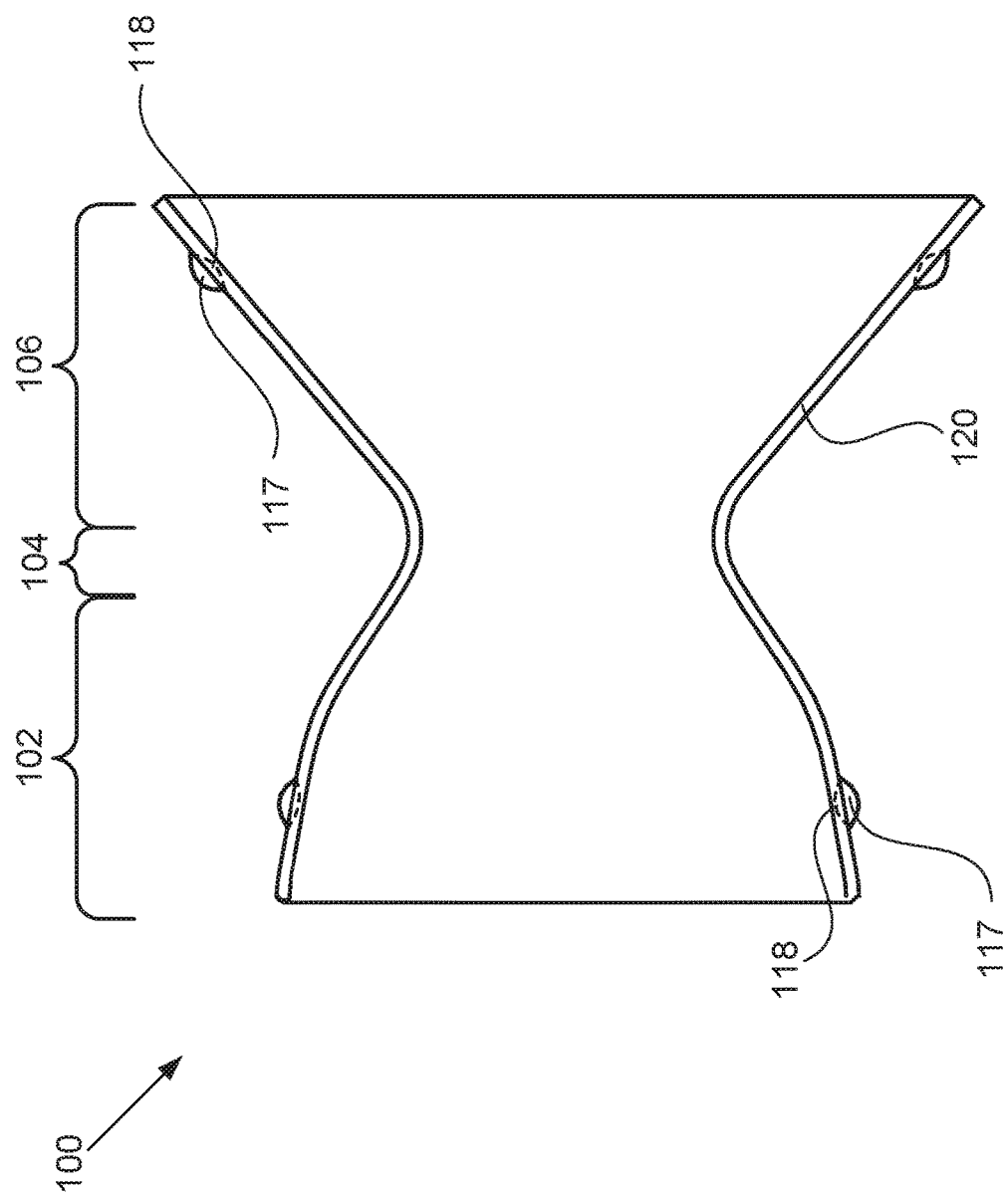

As illustrated in FIG. 1D, biocompatible material 120 may include one or more cavities 118, e.g., holes or grooves, disposed circumferentially along a surface of biocompatible material 120 such that one or more biodegradable rings 117 are disposed at least partially within the one or more cavities. Although FIG. 1D illustrates one or more cavities 118 disposed circumferentially along an outer surface of biocompatible material 120, as described above, any combination of one or more biodegradable rings 117 may be utilized to effectively reduce tissue overgrowth to preserve longevity and patency of device 100, and thus one or more cavities 118 may be disposed circumferentially along either or both an outer and/or inner surface of biocompatible material 120 to accommodate the biodegradable rings positioned along biocompatible material 120. In accordance with another aspect of the present invention, one or more cavities 118 may include a plurality of individual cavities of various shapes and sizes disposed in a circumferential pattern along the inner and/or outer surface of biocompatible material 120, such that the biodegradable material is disposed within the cavities and biodegrade to release the tissue overgrowth inhibiting drug in a ring-like manner.

Referring now to FIGS. 1E and 1F, the biodegradable material of device 100 may be in the form of a biodegradable material layer embedded within biocompatible material 120. For example, biocompatible material 120 may include first biocompatible material layer 121 and second biocompatible material layer 122 such that biodegradable material layer 119 is sandwiched in between the first and second biocompatible material layers of biocompatible material 120. Accordingly, first biocompatible material layer 121 and/or second biocompatible material layer 122 illustratively includes a plurality of nodal pores 123 sized and shaped to permit the drug to be released from biodegradable material layer 119, as biodegradable material layer 119 biodegrades, to permeate therethrough for inhibiting tissue overgrowth across nodal pores 123. Nodal pores 123 may be disposed in a circumferential pattern along first biocompatible material layer 121 and/or second biocompatible material layer 122 of biocompatible material 120 such that the tissue overgrowth inhibiting drug is released from biodegradable material 119 in a ring-like manner. Although FIG. 1E illustrates nodal pores 123 disposed within first biocompatible material layer 121, as will be understood by a person ordinarily skilled in the art, nodal pores 123 may be disposed within second biocompatible material layer 122, or a combination of both first and second biocompatible material layers.

Referring now to FIGS. 1G and 1H, the biodegradable material of device 100 may be embedded in stent 110. For example, ring 115 may include one or more depressions 124 formed on its surface, such that biodegradable material 125 is disposed within one or more depressions 124. One or more depressions 124 may include a plurality of individual cavities of various shapes and sizes disposed in a circumferential pattern along a ring of stent 110, such that biodegradable material 125 is disposed within the cavities and biodegrades to release the tissue overgrowth inhibiting drug in a ring-like manner about device 100. As illustrated in FIGS. 1G and 1H, one or more depressions 124 may be circular cavities disposed circumferentially along ring 115. Accordingly, the tissue overgrowth inhibiting drug may be released from biodegradable material 125 in a ring-like manner about device 100.

In accordance with another aspect of the present invention, one or more depressions 124 may include a single groove extending circumferentially along the surface of the ring, such that biodegradable material 125 is disposed within the groove in a closed ring shape about stent 110. Although FIGS. 1G and 1H illustrate one or more depressions 124 disposed along a surface of ring 115, as will be understood by a person ordinarily skilled in the art, one or more depressions 124 may be disposed on any of the rings of stent 110, e.g., rings 112, 113, 114, 115, or 116, to inhibit tissue overgrowth across the respective ring. In addition to or alternatively, one or more depressions 124 may be disposed along any one of longitudinal struts 111 of stent 110, such that the biodegradable material is disposed within the one or more depressions within the longitudinal struts.

Figure 1J:
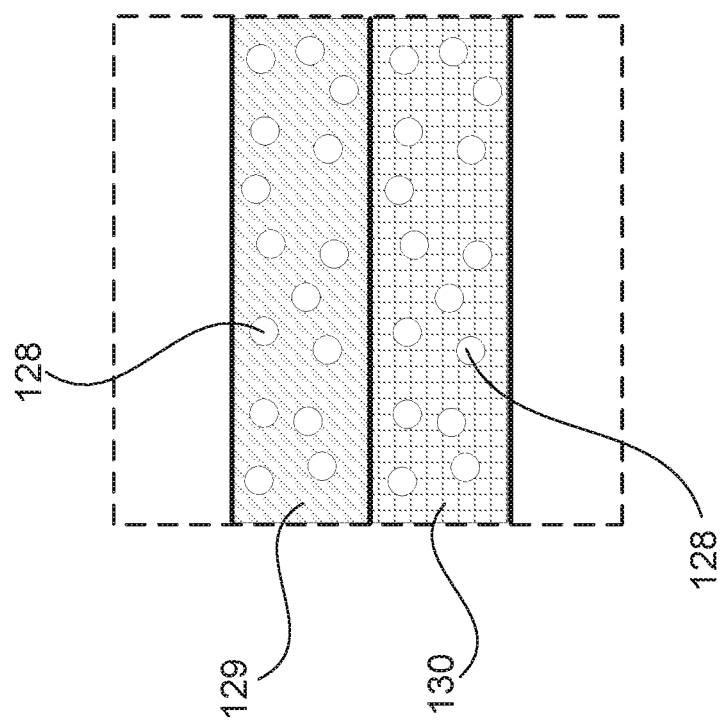
FIGS. 1I-1J illustrate exemplary drug-eluting biodegradable materials having multiple layers, according to some embodiments of the present invention.
Figure 1I:
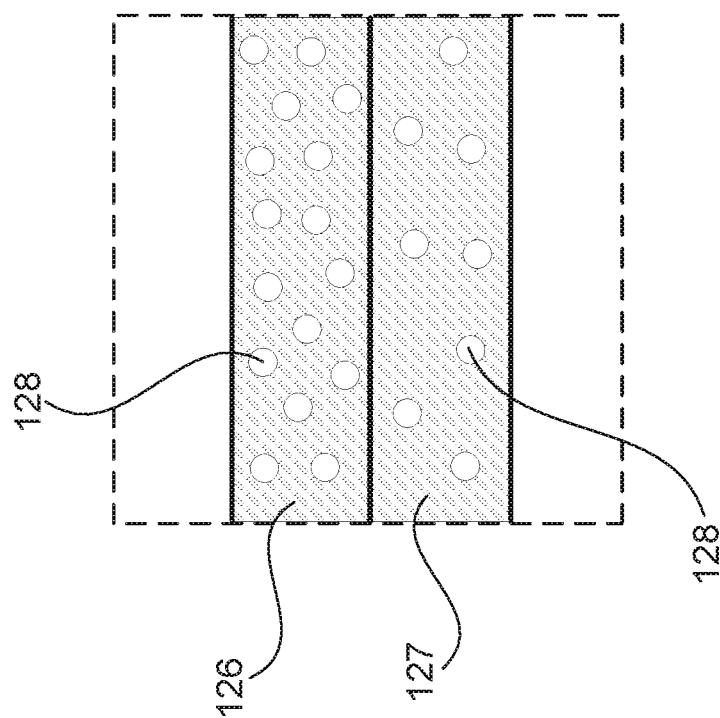

Referring now to FIGS. 1I and 1J, the biodegradable material of device 100 may include multiple layers of biodegradable materials. For example, as illustrated in FIG. 1I, the biodegradable material includes first biodegradable layer 126 and second biodegradable layer 127. First biodegradable layer 126 includes a first biodegradable material and a first concentration of drug 128 embedded therein such that the first concentration of drug 128 is released as the first biodegradable material biodegrades. Second biodegradable layer 127 includes a second biodegradable material and a second concentration of drug 126 embedded therein such that the second concentration of drug 126 is released as the second biodegradable material biodegrades. The drug in the first biodegradable material may be the same type of drug as the drug in the second biodegradable material or they may be different. The first and second biodegradable materials making up first biodegradable layer 126 and second biodegradable layer 127 may be the same. As shown in FIG. 1I, the second concentration of drug 128 is different from the first concentration of drug 128. Therefore, the concentration of drug 128 released from the biodegradable material may be selectively controlled. As will be understood by a person ordinarily skilled in the art, more than two layers of biodegradable materials may be used, e.g., three or four or more layers, such that each respective layer may include its own unique concentration and/or type of drug.

As illustrated in FIG. 1J, the biodegradable material includes first biodegradable layer 129 and second biodegradable layer 130. First biodegradable layer 129 and second biodegradable layer 130 may have the same concentration of drug 128; however, first biodegradable layer 129 may be selected such that it biodegrades at a first biodegradable rate, and second biodegradable layer 130 may be selected such that it biodegrades at a second biodegradable rate different from the first biodegradable rate of first biodegradable layer 129. Accordingly, the rate of drug 128 released may be selectively controlled.

As will be understood by a person ordinarily skilled in the art, the biodegradable materials having multiple layers of biodegradable materials as described with reference to FIGS. 1I and 1J may be used in any of the embodiments disclosed above with referenced to FIGS. 1B-1H.

In some embodiments, device 100 may include one or more biodegradable components that increase the cross-sectional area of the device so as to compensate for tissue overgrowth, which may occur over the first several weeks to months following implantation. For example, as illustrated in FIG. 1K, device 100 may include a layer of biodegradable substance 129 disposed on the inner surface of biocompatible material 120, in the neck and second flared end regions of device 100. Biodegradable substance layer 129 biodegrades or is bioresorbed gradually, for example over a period of a few weeks to a few months, thus increasing the cross-sectional flow area of device 100. However, during this same time period, tissue may overgrow on the interior surface of device 100 and thus may decrease the cross-sectional flow area of the device. Preferably, the rate at which biodegradable substance layer 129 degrades is approximately equal to the rate at which tissue overgrows on the interior surface of device 100, thus resulting in substantially uniform flow characteristics of the device over time.

Figure 1L:
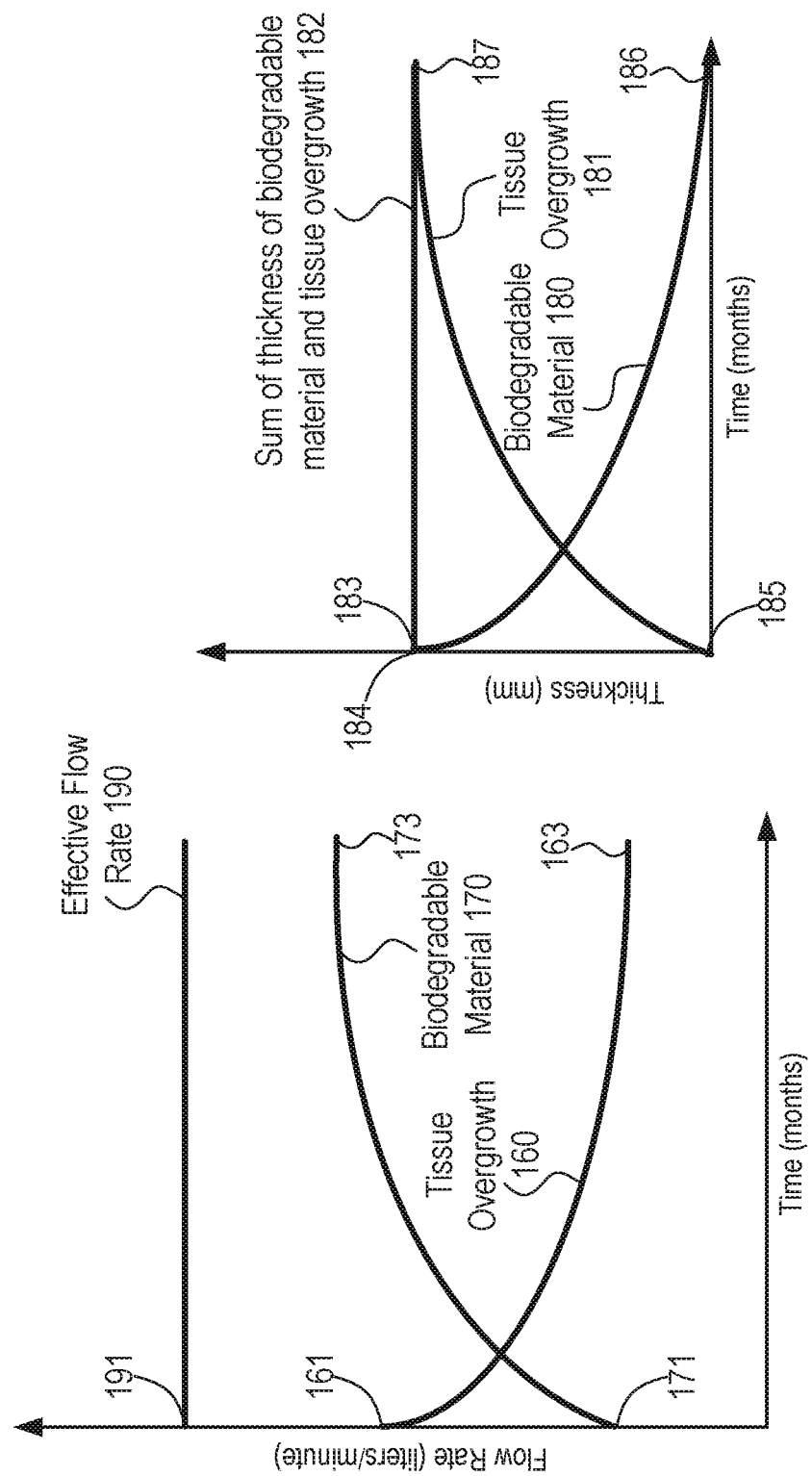
FIG. 1L is a plot schematically illustrating changes in flow rate over time through the device of FIG. 1K caused by tissue overgrowth, change in shunt cross-sectional area, and the overall effective flow rate through the device, and a plot schematically illustrating changes of thickness of the biodegradable material and tissue overgrowth on the device of FIG. 1K over time, and the sum of the thickness.

For example, FIG. 1L includes a plot schematically illustrating changes in flow rate (and cross-sectional area) through device 100 that are respectively caused by tissue overgrowth and biodegradation of layer 129, as well as the total effective flow rate through device 100. When the device 100 is initially implanted (time=0), the effective flow rate (cross-sectional flow area) 190 has an initial value of 191, which reflects that there is substantially no reduction in flow rate (cross-sectional flow area) caused by tissue overgrowth 160 (point 161), but a significant reduction in flow rate (cross-sectional flow area) caused by the layer of biodegradable substance 170 (point 171). Over time, the body resorbs or biodegrades the layer of biodegradable substance, causing a gradual increase in the flow rate attributable to this degradation 170, until substantially all of the biodegradable material is gone (point 173). Over a similar time period, tissue overgrowth causes a gradual decrease in flow rate attributable to this overgrowth 160, until the tissue overgrowth reaches a steady-state level (point 163). The collective effect of these two changes preferably is that the flow rate (and cross-sectional flow area) is maintained within a desired range over the first few weeks or months following device implantation, as well as thereafter.

FIG. 1L further includes a plot schematically illustrating changes of the thickness of biodegradable material 180 and the thickness of tissue overgrowth 181 on device 100 over the same time period discussed above, as well as the sum of the thickness of the biodegradable material and the tissue overgrowth 182 over that time. When device 100 is initially implanted (time=0), the thickness of biodegradable material 180 has an initial maximum value of 183, and the thickness of tissue overgrowth 181 has a minimum value 185, e.g., 0 mm. Thus the sum of the thickness of the biodegradable material and the tissue overgrowth 182 has an initial value of 184, which is equal to the initial thickness of biodegradable material 183. Over time, the body resorbs or biodegrades the layer of biodegradable substance, causing a gradual decrease in the thickness of biodegradable material 180, until substantially all of the biodegradable material is gone (point 186). Over a similar time period, tissue overgrowth increases causing an increase in the thickness of tissue overgrowth 181 until the tissue overgrowth reaches a steady-state level (point 187). The collective effect of these two changes preferably is that the sum of the thickness of the biodegradable material and the tissue overgrowth 182 is essentially constant over the first few weeks or months following device implantation, as well as thereafter.

Note that the actual rates of tissue overgrowth and material biodegradation may vary from subject to subject and even over time for the same subject, and that such rates need not be exactly equal to each other at all times (or even at any time), so long as the effective flow rate (cross-sectional area) of the device remains within acceptable parameters. For example, in some embodiments, beginning approximately one month after implantation the biodegradable material layer 129 illustrated in FIG. 1K is gradually replaced by tissue overgrowth (e.g., epithelial tissue or a neointimal layer), maintaining neck region 104 at a substantially constant diameter (e.g., tissue overgrowth causing a neck diameter decrease of about 0.4 mm and degradation of biodegradable substance causing a neck diameter increase of about 0.4 mm).

Referring again to FIG. 1K, biodegradable substance layer 129 may be formed of the same material as the biodegradable material described above with reference to FIGS. 1B-1J. For example, biodegradable substance layer 129 may comprise any suitable material that the body will gradually bioresorb or biodegrade, for example a hydrogel (e.g., polyethylene glycol hydrogel), synthetic polymer, or biological polymer. Examples of suitable synthetic polymers may include collagen-terpolymer; poly(lactic-co-glycolic) acids such as polylactic acid (PLA), poly L-lactic acid (PLLA), polyglycolic acid (PGA), and poly(lactic-co-glycolic) acid copolymer (PLGA); poly(ε-caprolactone); methacrylated dextran-aminoethyl methacrylate copolymer (Dex-MA/AEMA); polydiaxanone; and poly(glycerol sebacate) (PGS). Examples of suitable biological polymers may include polysialic acid (PSA), collagen type I/III, chitosan, and chitin. These materials are meant to be purely illustrative, and it should be appreciated that any suitable biodegradable or bioresorbable material may be used. Biodegradable substance layer 129 may have a thickness of 0.10 to 0.50 mm, e.g., 0.20 to 0.40 mm, e.g., about 0.30 mm, that reduces the rate of flow through device 100 to about 50-70% of what the flow rate would be without layer 129.

In addition, like the biodegradable material described above with reference to FIGS. 1B-1J, biodegradable substance layer 129 may have a drug, e.g., an -olimus drug, embedded therein that is released over time as the biodegradable substance layer bioresorbs or biodegrades. As the drug is released, tissue overgrowth is inhibited across the biodegradable substance layer.

As will be understood by a person ordinarily skilled in the art, any combination of the biodegradable materials described above with reference to FIGS. 1B-1J, e.g., one or more biodegradable rings 117, and biodegradable substance layer 129 may be utilized to effectively reduce tissue overgrowth to preserve longevity and patency of device 100. For example, FIG. 1M illustrates one or more holes 118 disposed on the outer surface of biocompatible material 120 adjacent the outlet end of first flared end region 102 of device 100, one or more holes 118 having one or more biodegradable rings 117 disposed therein, as well as biodegradable substance layer 129 disposed on the inner surface of biocompatible material 120, in the neck and second flared end regions of device 100.

It should be appreciated that not all embodiments need necessarily include biodegradable substance layer 129. However, it is believed that providing biodegradable substance layer 129 may further enhance the functionality of the inventive devices by further improving control over the flow characteristics of the devices over time, e.g., by compensating for changes in flow caused by tissue overgrowth.

As noted above, hourglass-shaped device 100 preferably is configured for implantation through the fossa ovalis of the atrial septum, particularly through the middle of the fossa ovalis. As known to those skilled in the art, the fossa ovalis is a thinned portion of the atrial septum caused during fetal development of the heart, which appears as an indent in the right side of the atrial septum and is surrounded by a thicker portion of the atrial septum. While the atrial septum itself may be several millimeters thick and muscular, the fossa ovalis may be only approximately one millimeter thick, and is formed primarily of fibrous tissue. Advantageously, because the fossa ovalis comprises predominantly fibrous tissue, that region of the atrial septum is not expected to undergo significant tension or contraction during the cardiac cycle, and thus should not impose significant radial stresses on stent 110 that could lead to stress-induce cracking. In addition, the composition of the fossa ovalis as primarily fibrous tissue is expected to avoid excessive endothelialization after implantation.

Figure 2A:
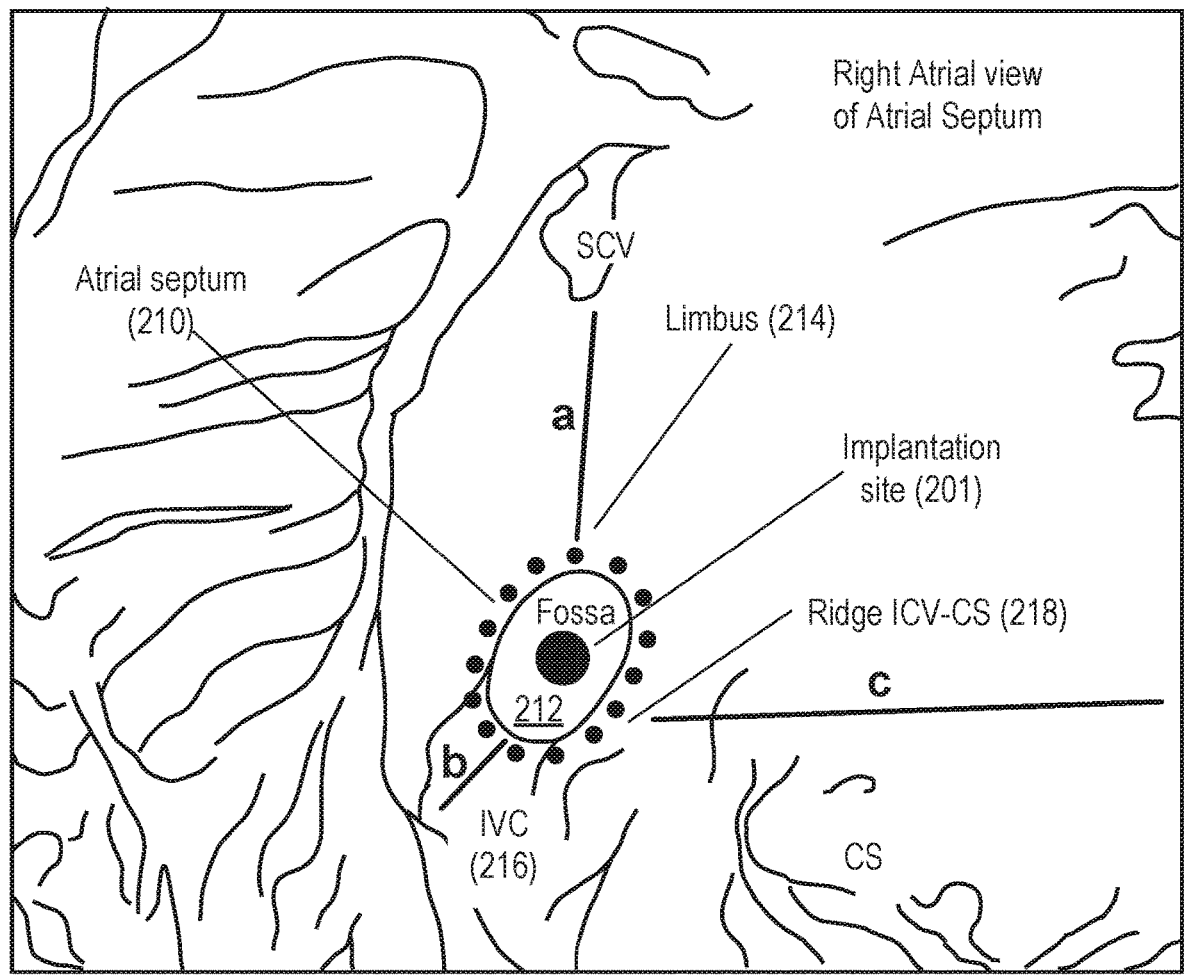
FIG. 2A schematically illustrates a plan view of the right atrial side of the atrial septum, including a site for implanting an hourglass-shaped device through the middle of the fossa ovalis.
Figure 2B:
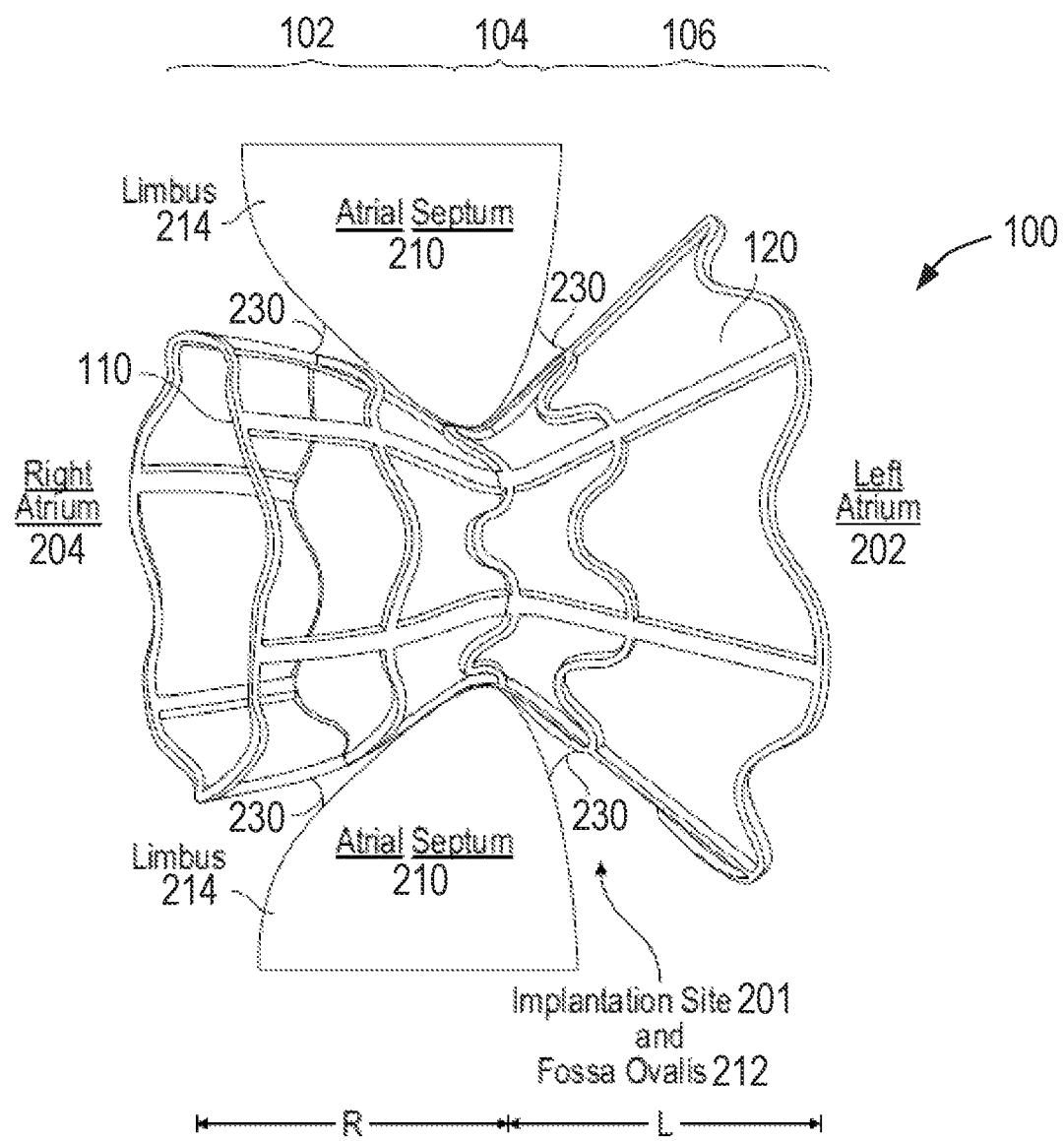
FIG. 2B schematically illustrates a perspective view of the hourglass-shaped device of FIGS. 1A-1E positioned in the fossa ovalis of the atrial septum, according to some embodiments of the present invention.

In some embodiments of the present invention, hourglass-shaped device 100 is asymmetrically shaped to take advantage of the natural features of atrial septum 210 near the fossa ovalis, and to provide suitable flow characteristics. FIG. 2A illustrates a plan view of the right atrial side of the atrial septum 210, including an implantation site 201 through the fossa ovalis 212. Preferably, the implantation site 201 is through the middle of the fossa ovalis 212, so that the device may be implanted at a spaced distance from the surrounding limbus 214, inferior vena cava (IVC) 216, and atrial wall 210. For example, as illustrated in FIG. 2B, first flared end region 102 is configured to be implanted in right atrium 204 and may be tapered so as to have a more cylindrical shape than does second flared end region 106, which is configured to be implanted in left atrium 202. The more cylindrical shape of first flared end region 102 may reduce or inhibit contact between first flared end region 102 and the limbus 214 of the fossa ovalis 212, that is, between first flared end region 102 and the prominent margin of the fossa ovalis, while still anchoring device 100 across atrial septum 210. The more cylindrical shape of first flared end region 102 further may reduce or inhibit contact between first flared end region 102 and the right atrial wall, as well as the ridge 218 separating the coronary sinus from the inferior vena cava (IVC) (shown in FIG. 2A but not FIG. 2B). Additionally, in some embodiments the first flared end region 102 substantially does not extend beyond the indent of the fossa ovalis in the right atrium, and therefore substantially does not restrict blood flow from the IVC 216.

In accordance with one aspect of the invention, device 100 preferably is configured so as to avoid imposing significant mechanical forces on atrial septum 210 or atria 202, 204, allowing the septum to naturally deform as the heart beats. For example, muscular areas of septum 210 may change by over 20% between systole and diastole. It is believed that any significant mechanical constraints on the motion of atrial septum 210 in such areas would lead to the development of relatively large forces acting on the septum and/or on atrial tissue that contacts device 100, which potentially would otherwise cause the tissue to have an inflammatory response and hyperplasia, and possibly cause device 100 to eventually lose patency. However, by configuring device 100 so that neck region may be implanted entirely or predominantly in the fibrous tissue of the fossa ovalis 212, the hourglass shape of device 100 is expected to be sufficiently stable so as to be retained in the septum, while reducing mechanical loads on the surrounding atrial septum tissue 210. As noted elsewhere herein, tissue overgrowth from atrial septum 210 in regions 230 may further enhance binding of device 100 to the septum.

Also, for example, as illustrated in FIG. 2B, neck region 104 of device 100 is significantly narrower than flared end regions 102, 106, facilitating device 100 to "self-locate" in a puncture through atrial septum 210, particularly when implanted through the fossa ovalis. In some embodiments, neck region 104 may have a diameter suitable for implantation in the fossa ovalis, e.g., that is smaller than the fossa ovalis, and that also is selected to inhibit blood flow rates exceeding a predetermined threshold. For example, the smallest diameter of neck 104 may be between about 3 and 6 mm, e.g., between about 4.5 mm and 5.5 mm, preferably between about 4.5 mm and 5.5 mm. For example, it is believed that diameters of less than about 4.5 mm may in some circumstances not allow sufficient blood flow through the device to decompress the left atrium, and may reduce long-term patency of device 100, while diameters of greater than about 5.5 mm may allow too much blood flow. For example, flow rates of greater than 1.2 liters/minute, or even greater than 1.0 liters/minute are believed to potentially lead to remodeling of the right atrium. Preferably, the effective diameter at the narrowest point in device 100, i.e., the narrowest diameter provided by the combination of neck 104 and biocompatible material 120 is about 4.5 mm to 4.8 mm. Such a diameter range is expected to provide a flow rate of about 0.80 liters/minute or less following overgrowth of septal tissue, which may anchor device 100 in place, and which may result in an overall diameter reduction of about 1.0 mm over time.

In some embodiments, the length of first flared end region 102 also may be selected to protrude into the right atrium by a distance selected to inhibit tissue overgrowth that may otherwise interfere with the operation of device 100. For example, distance R between the narrowest portion of neck region 104 and the end of first flared region 102 may be approximately 5.0 to 9.0 mm, for example about 5.5 to about 7.5 mm, or about 6 mm, so as not to significantly protrude above the limbus of fossa ovalis 212. Second flared end region 106 preferably does not significantly engage the left side of atrial septum 210, and distance L may be between 2.0 and 6.0 mm, for example about 2.5 to 7 mm, or about 3.0 mm. It is believed that configuring first and second flared end regions 102, 106 so as to extend by as short a distance as possible into the right and left atria, respectively, while still maintaining satisfactory flow characteristics and stabilization in atrial septum 210, may reduce blockage of flow from the inferior vena cava (IVC) in the right atrium and from the pulmonary veins in the left atrium. In one illustrative embodiment, distance R is about 6.0 mm and distance L is about 3.0 mm. In some embodiments, the overall dimensions of device 100 may be 10-20 mm long (L+R, in FIG. 2B), e.g., about 12-18 mm, e.g., about 14-16 mm, e.g., about 15 mm.

The diameters of the first and second flared end regions further may be selected to stabilize device 100 in the puncture through atrial septum 210, e.g., in the puncture through fossa ovalis 212. For example, first flared end region 102 may have a diameter of 10-15 mm at its widest point, e.g., about 9.0-13 mm; and second flared end region 106 may have a diameter of 10-20 mm at its widest point, e.g., about 13-15 mm. The largest diameter of first flared end region 102 may be selected so as to avoid mechanically loading the limbus of the fossa ovalis 212, which might otherwise cause inflammation. The largest diameter of second flared end region 106 may be selected so as to provide a sufficient angle between first and second flared end regions 102, 106 to stabilize device 100 in the atrial septum, while limiting the extent to which second flared end region 106 protrudes into the left atrium (e.g., inhibiting interference with flow from the pulmonary veins), and providing sufficient blood flow from the left atrium through neck region 104. In one embodiment, the angle between the first and second flared end regions is about 50-90 degrees, e.g., about 60 to 80 degrees, e.g., about 70 degrees. Such an angle may stabilize device 100 across the fossa ovalis, while inhibiting excessive contact between the device and the atrial septum. Such excessive contact might cause inflammation because of the expansion and contraction of the atrial septum during the cardiac cycle, particularly between diastole and systole. In one embodiment, the first flared end region subtends an angle of approximately 80 degrees, that is, the steepest part of the outer surface of the first flared end region is at an angle of approximately 40 degrees relative to a central longitudinal axis of the device. The second flared end region may subtend an angle of approximately 75 degrees, that is, the steepest part of the outer surface of the second flared end region is at an angle of approximately 37.5 degrees relative to the central longitudinal axis of the device.

When device 100 is implanted across the atrial septum, as illustrated in FIG. 2B, left atrial pressures may be regulated in patients having congestive heart failure (CHF). For example, device 100 may reduce pressure in the left atrium by about 2-5 mmHg immediately following implantation. Such a pressure reduction may lead to a long-term benefit in the patient, because a process then begins by which the lowered left atrial pressure reduces the transpulmonary gradient, which reduces the pulmonary artery pressure. However, the right atrial pressure is not significantly increased because the right atrium has a relatively high compliance. Furthermore, the pulmonary capillaries may self-regulate to accept high blood volume if needed, without increasing pressure. When the left atrial pressure is high, the pulmonary capillaries constrict to maintain the transpulmonary gradient, but as the left atrial pressure decreases, and there is more blood coming from the right atrium, there are actually higher flow rates at lower pressures passing through the pulmonary circulation. After a period of between a few hours and a week following implantation of device 100, the pulmonary circulation has been observed to function at lower pressures, while the systemic circulation maintains higher pressures and thus adequate perfusion. The resulting lower pulmonary pressures, and lower left ventricle end diastolic pressure (LVEDP) decrease the after load by working at lower pressures, resulting in less oxygen demand and less resistance to flow. Such small decreases in afterload may dramatically increase the cardiac output (CO) in heart failure, resulting in increased ejection fraction (EF). Moreover, because of the release in the afterload and in the pressures of the pulmonary circulation, the right atrial pressure decreases over time as well. Following myocardial infarction, the effect is even more pronounced, because the period after the infarction is very important for the remodeling of the heart. Specifically, when the heart remodels at lower pressures, the outcome is better.

In the region of contact between device 100 and atrial septum 210, preferably there is limited tissue growth. The connective tissue of atrial septum 210 is non-living material, so substantially no nourishing of cells occurs between the septum and device 100. However, local stagnation in flow may lead to limited cell accumulation and tissue growth where device 100 contacts atrial septum 210, for example in regions designated 230 in FIG. 2B. Such tissue growth in regions 230 may anchor device 210 across atrial septum 210. Excessive tissue growth beyond regions 230 on device 100 may be inhibited via one or more drug-eluting biodegradable rings disposed adjacent neck region 104 of device 100.

Additionally, such tissue growth may cause the flow between the external surface of device 100 and atrial septum 210 to become smoother and more continuous, thus reducing or inhibiting further cell accumulation and tissue growth in regions 230. Flow reductions caused by such tissue growth may be offset by providing in the device a biodegradable substance that biodegrades over time, as discussed above with respect to FIGS. 1K-1L. Furthermore, as noted above, first flared end region 102 of stent 110 preferably is bare metal. This configuration is expected to inhibit formation of stagnation points in blood flow in right atrium 204, that otherwise may lead to excessive tissue growth on device 100.

A method 300 of making device 100 illustrated in FIGS. 1A-1K and FIG. 2B will now be described with respect to FIG. 3. First, a tube of shape-memory material, e.g., a shape-memory metal such as nickel titanium (NiTi), also known as NITINOL, is provided (step 301 of FIG. 3). Other suitable materials known in the art of deformable stents for percutaneous implantation may alternatively be used, e.g., other shape memory alloys, polymers, and the like. In one embodiment, the tube has a thickness of 0.25 mm.

Then, the tube is laser-cut to define a plurality of rings, e.g., sinusoidal rings, connected by longitudinally extending struts (step 302). For example, struts 111 and sinusoidal rings 112-116 illustrated in FIG. 1A may be defined using laser cutting a single tube of shape-memory metal, and thus may form an integral piece of unitary construction. Alternatively, struts 111 and sinusoidal rings 112-116 may be separately defined from different pieces of shape-memory metal and subsequently coupled together.

Referring again to FIG. 3, the laser-cut tube then is expanded on a mandrel to define first and second flared end regions and a neck therebetween, e.g., to define first end region 102, second end region 106, and neck region 104 as illustrated in FIG. 1A; the expanded tube then may be heated to set the shape of stent 110 (step 303). In one example, the tube is formed of NITINOL, shaped using a shape mandrel, and placed into an oven for 11 minutes at 530 C to set the shape. Optionally, the stent thus defined also may be electropolished to reduce thrombogenicity, or otherwise suitably treated. Such electropolishing may alternatively be performed at a different time, e.g., before shaping using the mandrel.

Figure 3:
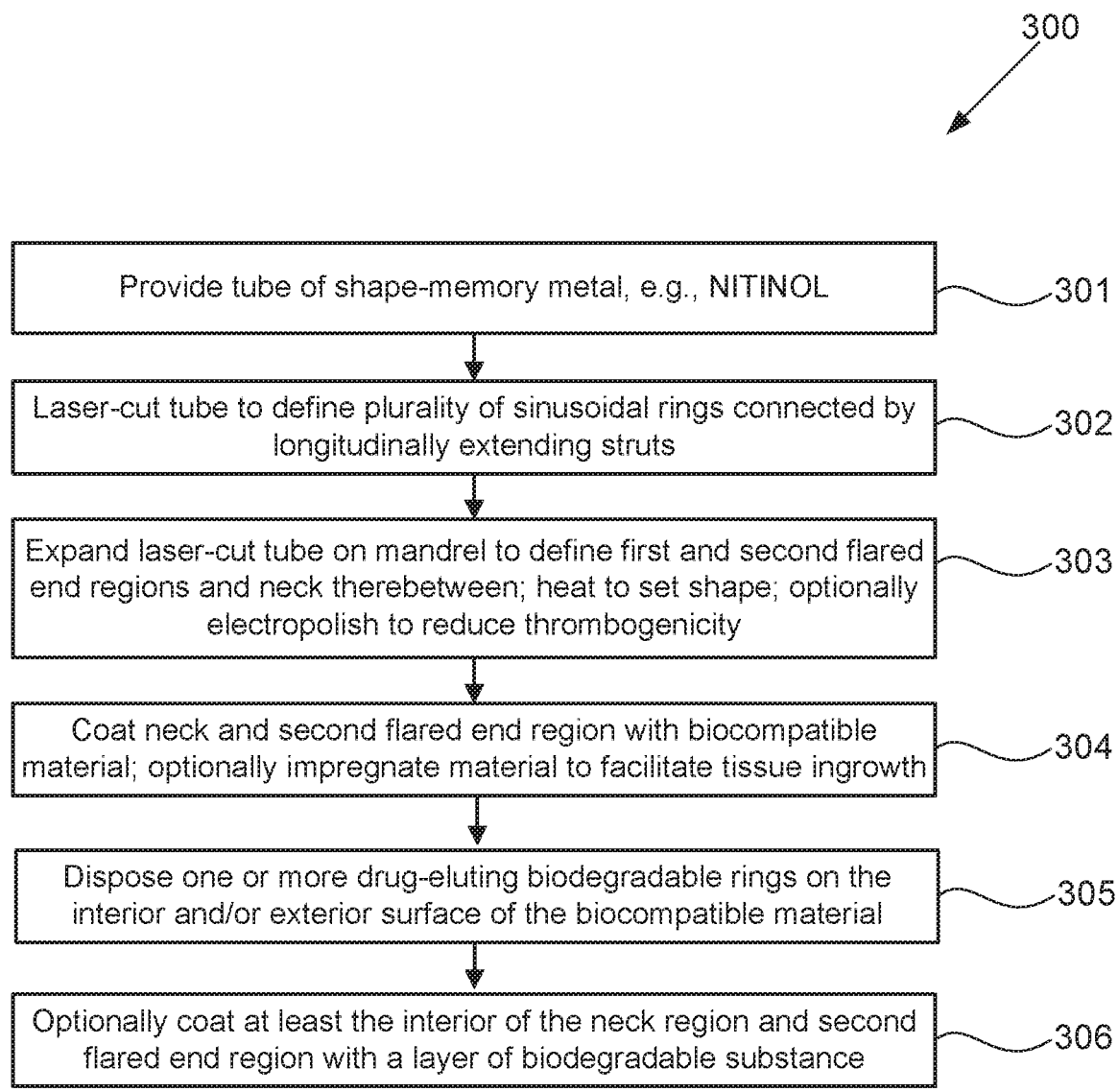
FIG. 3 is a flow chart of steps in a method of making an hourglass-shaped device, according to some embodiments of the present invention.

As shown in FIG. 3, the neck and second flared end region of the stent then may be coated with a biocompatible material (step 304). Examples of suitable biocompatible materials include expanded polytetrafluoroethylene (ePTFE), polyurethane, DACRON (polyethylene terephthalate), silicone, polycarbonate urethane, and animal pericardial tissue, e.g., from an equine, bovine, or porcine source. In one embodiment, the stent is coated with the biocompatible material by covering the inner surface of the stent with a first sheet of ePTFE, and covering the outer surface of the stent with a second sheet of ePTFE. The first and second sheets first may be temporarily secured together to facilitate the general arrangement, e.g., using an adhesive, suture, or weld, and then may be securely bonded together using sintering to form a strong, smooth, substantially continuous coating that covers the inner and outer surfaces of the stent. Portions of the coating then may be removed as desired from selected portions of the stent, for example using laser-cutting or mechanical cutting. For example, as shown in FIG. 1A, biocompatible material 120 may cover stent 110 between sinusoidal ring 113 and sinusoidal ring 116, i.e., may cover neck region 104 and second flared end region 106, but may be removed between sinusoidal ring 113 and sinusoidal ring 112, i.e., may be removed from (or not applied to) first flared end region 102.

In accordance with one aspect of the present invention, as described above, a plurality of cavities, e.g., holes or grooves, may be carved into at least one of sinusoidal rings 112, 113, 114, 115, 116, and/or longitudinal struts 111, such that a biodegradable material may be disposed therein.

The biocompatible material facilitates funneling of blood from the left atrium to the right atrium by providing a substantially smooth hemodynamic profile on both the inner and outer surfaces of device 100. Advantageously, this configuration is expected to inhibit the formation of eddy currents that otherwise may cause emboli to form, and facilitates smooth attachment of the device to the atrial septum, e.g., fossa ovalis. Biocompatible material 120 preferably is configured so as to direct blood flow from the left atrium through neck region 104 and into the right atrium. Biocompatible material 120 preferably also is configured so as to inhibit tissue growth from atrial septum 210 and surrounding tissue into device 100. In some embodiments, the biocompatible material 120 has a porosity that is preselected to allow limited cell growth on its surface; the cells that grow on such a surface preferably are endothelial cells that are exposed to blood and inhibit blood from coagulating on the biocompatible material. After such cells grow on the biocompatible material 120, the material preferably is substantially inert and thus not rejected by the body. Optionally, the biocompatible material may be impregnated with a second material that facilitates tissue ingrowth, e.g., carbon. Such impregnation may be performed before or after applying the biocompatible material to the stent.

In accordance with one aspect of the present invention, as described above, biocompatible material 120 may have a biodegradable material layer embedded therein, wherein biocompatible material 120 has a plurality of nodal pores disposed on either or both upper and lower surfaces of biocompatible material 120.

Then, as shown in FIGS. 1B-1D, one or more biodegradable rings may be disposed on the interior and/or exterior surface of biocompatible material 120, such that the rings bioresorb or biodegrade over time to release a drug that inhibits tissue overgrowth across the rings (step 305). For example, as shown in FIG. 1D, a plurality of cavities, e.g., holes or grooves, may be carved into biocompatible material 120 such that the one or more biodegradable rings are disposed at least partially in the plurality of holes or grooves. Such carving may be performed before or after applying the biocompatible material to the stent.

The interior of the neck region and second flared end region then may be coated with a layer of biodegradable substance (306). For example, referring to FIG. 1K, biodegradable substance layer 129 may be disposed on biocompatible material 120 using any suitable technique, for example, using deep molding, spraying, or electrospinning. Note that if deep molding is used, any surfaces on which it is not desired to apply biodegradable substance layer 129 may be masked to avoid inadvertent deposition on such surfaces.

Figure 4:
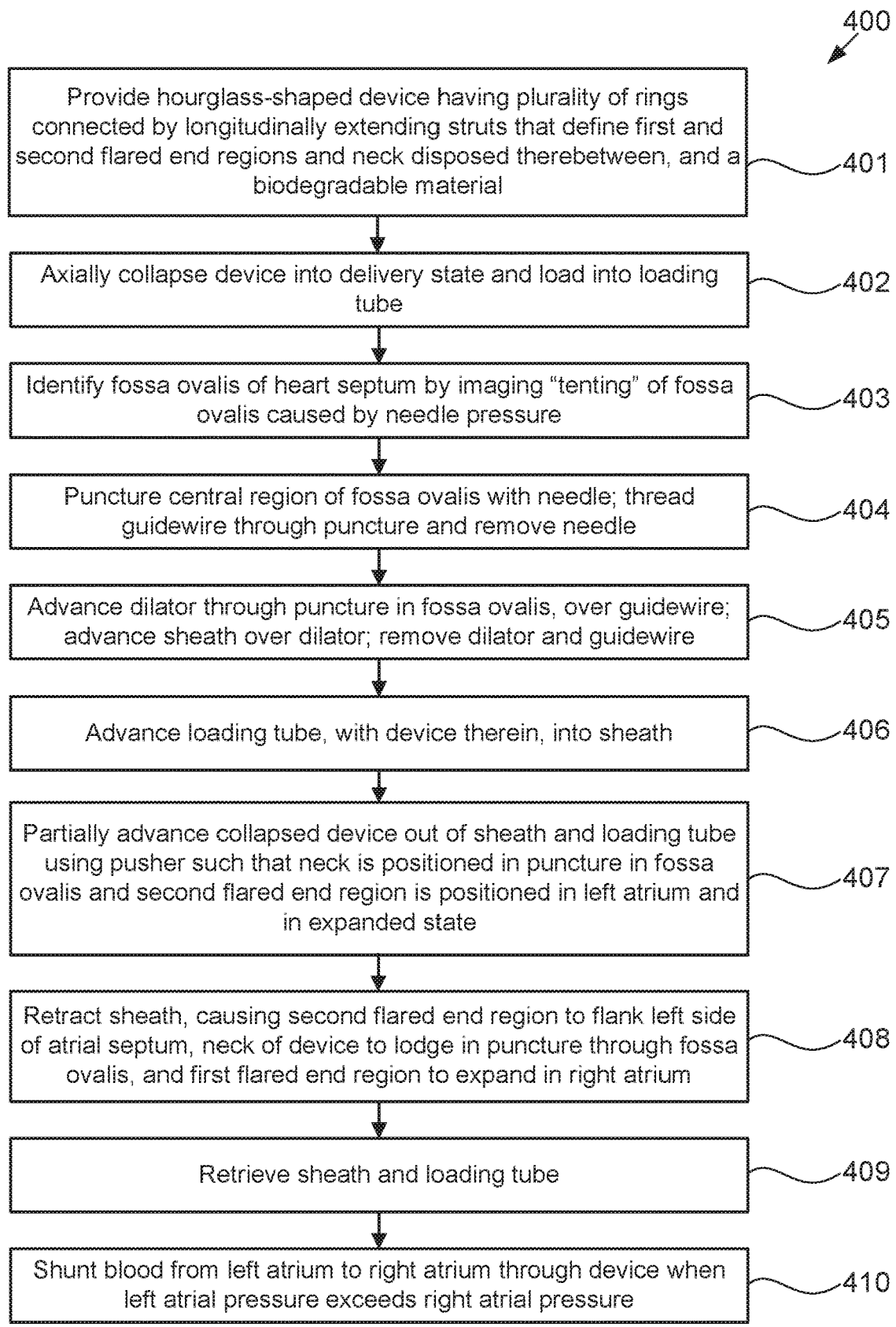
FIG. 4 is a flow chart of steps in a method of percutaneously implanting the hourglass-shaped device of FIGS. 1A-1E in a puncture through the fossa ovalis, according to some embodiments of the present invention.

A method 400 of using device 100 illustrated in FIGS. 1A-1K to reduce left atrial pressure in a subject, for example, a human having CHF, will now be described with reference to FIG. 4. Some of the steps of method 400 may be further elaborated by referring to FIGS. 5A-5D.

First, an hourglass-shaped device having a plurality of rings connected by longitudinally extending struts that define first and second flared end regions and a neck disposed therebetween, a biodegradable material, e.g., one or more drug-eluting biodegradable rings, and optionally a biodegradable substance layer, is provided (step 401). Such a device may be provided, for example, using method 300 described above with respect to FIG. 3.

Figure 5A:
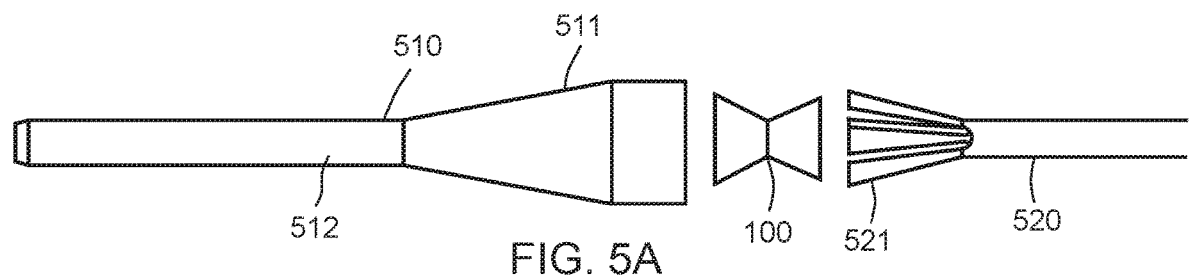
FIGS. 5A-5D schematically illustrate steps taken during the method of FIG. 4, according to some embodiments of the present invention.
Figure 5B:
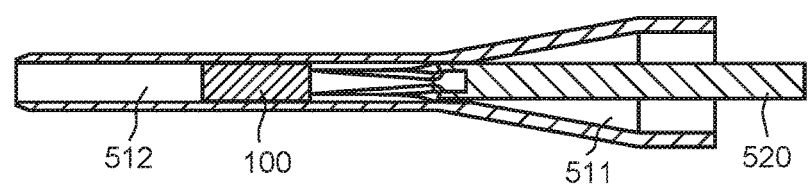

Then, the device is collapsed radially to a contracted delivery state, and loaded into a loading tube (step 402). For example, as illustrated in FIGS. 5A-5B, device 100 may be loaded into loading tube 510 using pusher 520 having "star"-shaped end 521. Loading tube 510 includes tapered loading end 511, which facilitates radial compression of device 100 into lumen 512 having a suitable internal diameter. Once device 100 is loaded into lumen 512, pusher 520 is retracted. Preferably, device 100 is loaded into loading tube 510 shortly before implantation, so as to avoid unnecessarily compressing device 100 or re-setting of the closed shape of leaflets 132, which may interfere with later deployment or operation of the device. In some embodiments, loading tube 510 has a diameter of 16 F or less, or 14 F or less, or 10 F or less, or 6 F or less, e.g., about 5 F, and device 100 has a crimped diameter of 16 F or less, or 14 F or less, or 10 F or less, or 6 F or less, e.g., about 5 F. In one illustrative embodiment, loading tube has a diameter of 15 F and device 100 has a crimped diameter of 14 F.

Figure 5C:
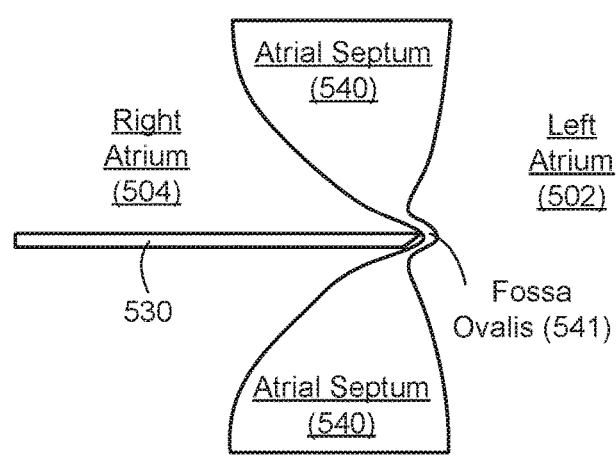

Referring again to FIG. 4, the device then is implanted, first by identifying the fossa ovalis of the heart septum, across which device 100 is to be deployed (step 403). Specifically, a BROCKENBROUGH needle may be percutaneously introduced into the right atrium via the subject's venous vasculature, for example, via the femoral artery. Then, under fluoroscopic or echocardiographic visualization, the needle is pressed against the fossa ovalis, at a pressure insufficient to puncture the fossa ovalis. As illustrated in FIG. 5C, the pressure from needle 530 causes "tenting" of fossa ovalis 541, i.e., causes the fossa ovalis to stretch into the left atrium. Other portions of atrial septum 540 are thick and muscular, and so do not stretch to the same extent as the fossa ovalis. Thus, by visualizing the extent to which different portions of the atrial septum 540 tents under pressure from needle 530, fossa ovalis 541 may be identified, and in particular the central portion of fossa ovalis 541 may be located.

Referring again to FIG. 4, the fossa ovalis (particularly its central region) may be punctured with the BROCKENBROUGH needle, and a guidewire may be inserted through the puncture by threading the guidewire through the needle and then removing the needle (step 404, not illustrated in FIG. 5). The puncture through the fossa ovalis then may be expanded by advancing a dilator over the guidewire. Alternatively, a dilator may be advanced over the BROCKENBROUGH needle, without the need for a guidewire. The dilator is used to further dilate the puncture and a sheath then is advanced over the dilator and through the fossa ovalis; the dilator and guidewire or needle then are removed (step 405, not illustrated in FIG. 5). The loading tube, with device 100 disposed in a contracted delivery state therein, then is advanced into the sheath (step 406, not illustrated in FIG. 5).

Figure 5D:
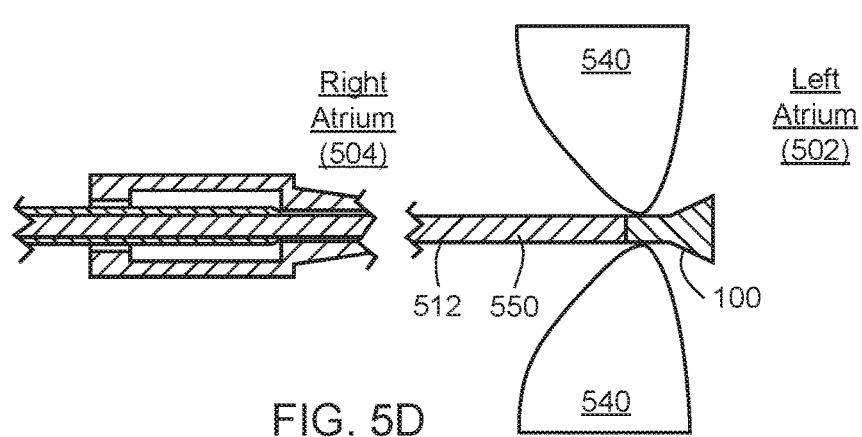

The device then is advanced out of the loading tube and into the sheath using a pusher, and then partially advanced out of the sheath, such that the second flared end of the device protrudes out of the sheath and into the left atrium, and expands to its deployed state (step 407). For example, as illustrated in FIG. 5D, pusher 550 may be used to partially advance device 100 out of sheath 512 and into left atrium 502, which causes the second flared end region to expand in the left atrium. The pusher may be configured such that it cannot advance the device 100 completely out of the sheath, but instead may only push out the side of the device to be disposed in the left atrium, that is, the second flared end region. After the pusher advances the second flared end region out of the sheath, the pusher may be mechanically locked from advancing the device out any further. For example, an expanded region may be disposed on the end of the pusher proximal to the physician that abuts the sheath and prevents further advancement of the pusher after the second flared end region is advanced out of the sheath. The device then may be fully deployed by pulling the sheath back, causing the second flared end region of the device to engage the left side of the atrial septum. Such a feature may prevent accidentally deploying the entire device in the left atrium.

The sheath then is retracted, causing the second flared end region to flank the left side of the atrial septum and the neck of the device to lodge in the puncture through the fossa ovalis, and allowing expansion of the first flared end of the device into the right atrium (step 408, see also FIG. 2B). Any remaining components of the delivery system then may be removed, e.g., sheath, and loading tube (step 409). Once positioned in the fossa ovalis, the device shunts blood from the left atrium to the right atrium when the left atrial pressure exceeds the right atrial pressure (step 410), thus facilitating treatment and/or the amelioration of symptoms associated with CHF. Tissue overgrowth may be reduced or inhibited on the device by biodegrading the biodegradable material, e.g., the one or more biodegradable rings or any of the biodegradable materials described above, to release an -olimus drug, for example as discussed above with reference to FIGS. 1B-1D. In addition, the cross-sectional flow area (flow rate) of the device then may be maintained within a desired range by biodegrading the biodegradable substance layer to offset a decrease in the cross-sectional flow area (flow rate) caused by tissue overgrowth, for example as discussed above with reference to FIGS. 1K-1L. Alternatively, the cross-sectional flow area (flow rate) of the device then may be gradually increased by biodegrading the biodegradable substance layer over time.

In accordance with another aspect of the present invention, device 100 may include one or more layers of degradable components that may activated to selectively increase the cross-sectional area of the device to adapt to the needs of the patient based on the necessary flow pattern required for the patient. For example, when the clinical condition of the patient at some point after initial implantation of the interatrial shunt requires a greater flow pattern, e.g., from the left atrium to the right atrium, the diameter of the neck region of the shunt may be increased by causing the one or more layers of degradable components at the neck region to degrade, e.g., via applying heat or a degradation activating material to the one or more layers of degradable components, without having to increase the hole within the fossa ovalis.

Figure 6A:
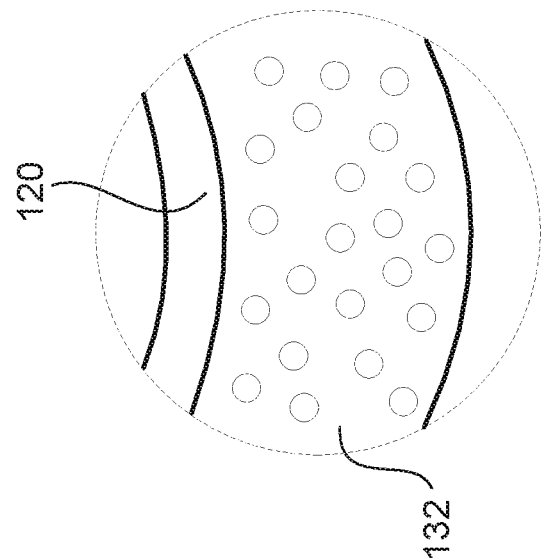
Figure 6A:
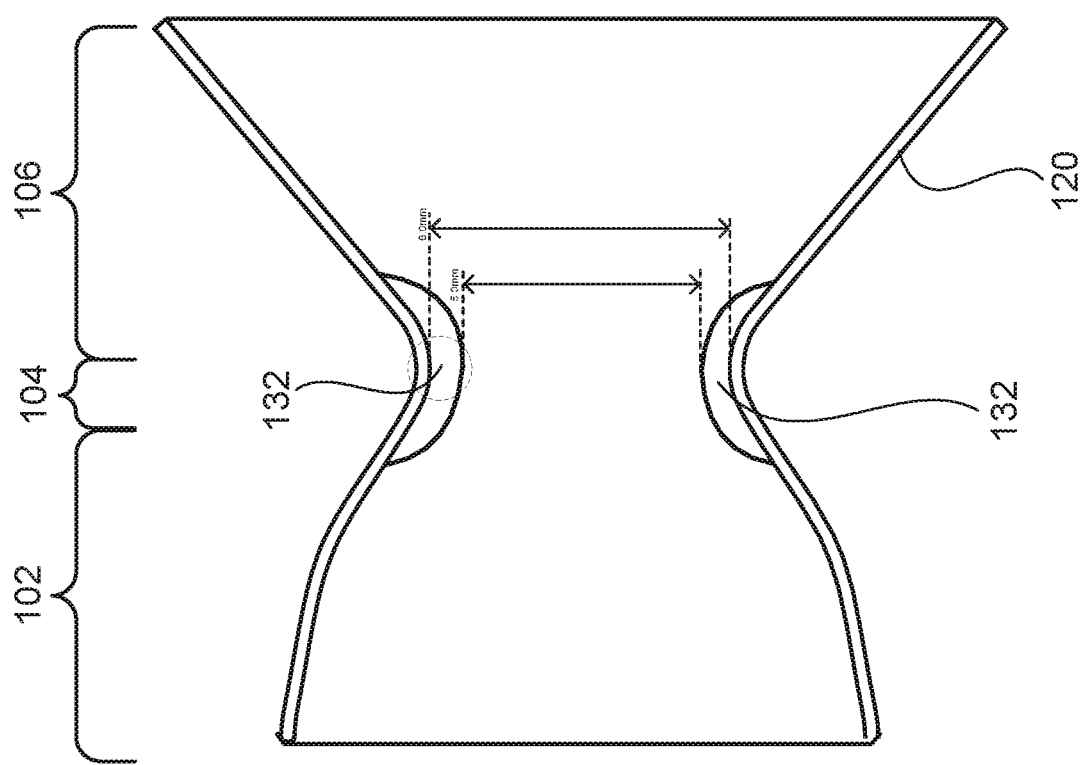

For example, as illustrated in FIG. 6A, device 100 may include a layer of degradable components 132 disposed on the inner surface of biocompatible material 120, in the neck region of device 100. As shown in FIG. 6A, the diameter at the neck region of device 100, e.g., the diameter of the distance between the inner surface of biocompatible material 120 on the stent frame, is 6.0 mm, and with the layer of degradable components 132 disposed thereon, the diameter of the passageway through device 100 at its neck region is 5.0 mm. Accordingly, the layer of degradable components 132 may have a thickness of 1.0 mm.

As shown in FIG. 6B, the layer of degradable components 132 is made of a degradable material that stays intact until exposed to an external stimulus. Thus, upon interaction with the stimulus, the layer of degradable components 132 will degrade, thereby increasing the cross-sectional area of the passageway through device 100 at its neck region. For example, when it is determined that the patient requires a larger flow pattern from the left atrium to the right atrium, a delivery balloon may be delivered and positioned within the passageway of device 100 adjacent to the layer of degradable components 132, and a heated contrast-water mixture may be delivered to the balloon to transmit heat to the layer of degradable components 132. The layer of degradable components 132 will degrade in response to the transmitted heat. Additionally, or alternatively, a biocompatible degradation activating material may be ejected adjacent to the layer of degradable components 132, thereby causing the layer of degradable components 132 to degrade. Upon complete degradation of the layer of degradable components 132, the diameter of the passageway through device 100 at its neck region will be 6.0 mm.

As will be understood by a person ordinarily skilled in the art, any combination of the biodegradable materials described above with reference to FIGS. 1B-1J, e.g., one or more biodegradable rings 117, and the layer of degradable components 132 may be utilized to effectively reduce tissue overgrowth to preserve longevity and patency of device 100.

Referring now to FIGS. 7A and 7B, device 100 may have two or more layers of degradable components, e.g., layer 132a and 132b, disposed on its neck region. Like the layer of degradable components 132, layers 132a and 132b may remain intact until exposed to external stimuli. Layers 132a may be made of degradable material that is different from the degradable material that form layer 132b, such that each of layers 132a and 132b are degradable in response to different stimuli. For example, as shown in FIG. 7A, the diameter at the neck region of device 100, e.g., the diameter of the distance between the inner surface of biocompatible material 120 on the stent frame, is 6.0 mm, and with the layer of degradable components 132b disposed thereon, the diameter of the passageway through device 100 at its neck region is 5.5 mm, and with the layer of degradable components 132a disposed thereon, the diameter of the passageway through device 100 at its neck region is 5.0 mm. Accordingly, the layer of degradable components 132b may have a thickness of 0.5 mm, and the layer of degradable components 132a may have a thickness of 0.5 mm. Thus, when it is determined that the patient requires a larger flow pattern from the left atrium to the right atrium, upon interaction with the first stimulus, e.g., a heated balloon or a biocompatible degradation activating material, the layer of degradable components 132a will degrade, thereby increasing the cross-sectional area of the passageway through device 100 at its neck region from 5.0 mm to 5.5 mm.

When it is determined that the patient requires an even larger flow pattern from the left atrium to the right atrium, a second stimulus may be introduced to cause the layer of degradable components 132b to degrade, thereby increasing the cross-sectional area of the passageway through device 100 at its neck region from 5.5 mm to 6.0 mm. As will be understood by a person having ordinary skill in the art, more than two layers of degradable components may be disposed at the neck region of device 100, each having a preselected thickness and each responding to the same or different stimuli, such that upon exposure to the corresponding stimulus, each layer of degradable components will degrade to selectively increase the cross-sectional area of the passageway through device 100 at its neck region.

The devices and methods described herein may be used to regulate left atrial pressures in patients having a variety of disorders, including congestive heart failure (CHF), as well as other disorders such as patent foramen ovale (PFO), or atrial septal defect (ASD). The devices and methods also may be used to reduce symptoms and complications associated with such disorders, including myocardial infarction. It is believed that patients receiving the device may benefit from better exercise tolerance, less incidence of hospitalization due to acute episodes of heart failure, and reduced mortality rates.

Devices constructed and implanted according to the present invention may provide for significantly improved mortality rates in subjects suffering from heart failure. In particular, the devices may significantly enhance ejection fraction, fractional shortening, and/or cardiac output in subjects who would otherwise have significantly diminished cardiac function as a result of excessive left atrial and left ventricular pressures. For example, subjects may be classified under the New York Heart Association (NYHA) classification system as having Class II (Mild) heart failure, who have slight limitation of physical activity and are comfortable at rest, but for whom ordinary physical activity results in fatigue, palpitation, or dyspnea; Class III (Moderate) heart failure, who have marked limitation of physical activity, may be comfortable at rest, and may experience fatigue, palpitation, or dyspnea if they engage in less than normal activity; or as having Class IV (Severe) heart failure, who are unable to carry out any physical activity without discomfort, exhibit symptoms of cardiac insufficiency at rest, and have increased discomfort if they undertake any physical activity. The present devices may significantly increase the cardiac output of such class III or class IV subjects, particularly those with low ejection fraction, enabling them to engage in significantly more physical activity than they otherwise could. The present devices further may decrease pulmonary artery pressure in subjects with left heart failure, and additionally may reduce or inhibit pulmonary congestion in patients with pulmonary congestion resulting from such heart failure, for example by inhibiting episodes of acute pulmonary edema. Indeed, as the above-described Example illustrates, the inventive device may reduce LAP and PAP significantly relative to what those pressures would otherwise be; such pressure reductions may not only provide immediate relief from acute symptoms, but further may facilitate cardiac remodeling over the weeks following implant and thus provide for enhanced cardiac function. The devices may in some embodiments include means for measuring the various parameters of interest, e.g., means such as discussed above with respect to the animal trials. Furthermore, it is believed that disposing one or more drug-eluting biodegradable rings on the interior and/or exterior surface of the biocompatible material covering the stent, such as one or more biodegradable rings 117 illustrated in FIGS. 1B-1D, will enhance the functionality of the device by reducing tissue overgrowth. Additionally, it is believed that providing a biodegradable substance layer, such as layer 129 illustrated in FIG. 1K, may further enhance the functionality of the device by improving control over flow rate e.g., by compensating for changes in flow caused by tissue overgrowth.

It should be noted that the inventive devices also may be used with patients having disorders other than heart failure. For example, in one embodiment the device may be implanted in a subject suffering from myocardial infarction, for example in the period immediately following myocardial infarction (e.g., within a few days of the event, or within two weeks of the event, or even within six months of the event). During such a period, the heart remodels to compensate for reduced myocardial function. For some subjects suffering from severe myocardial infarction, such remodeling may cause the function of the left ventricle to significantly deteriorate, which may lead to development of heart failure. Implanting an inventive device during the period immediately following myocardial infarction may inhibit such deterioration in the left ventricle by reducing LAP and LVEDP during the remodeling period. For example, in the above-described Example, heart failure was induced in the sheep by injecting microspheres that block the coronary artery and induce myocardial infarction. Following the myocardial infarction, the sheep developed heart failure. As can be seen in the various results for the implanted animals, implanting the inventive device even a week following the myocardial infarction inhibited degradation of the heart and yielded significantly improved mortality rates and cardiac functioning both immediately and over time as the subjects' hearts remodeled. As such, it is believed that implanting an inventive device for even a few weeks or months following myocardial infarction may provide significant benefits to the subject as their heart remodels. The device optionally then may be removed.

While various illustrative embodiments of the invention are described above, it will be apparent to one skilled in the art that various changes and modifications may be made herein without departing from the invention. It will further be appreciated that the devices described herein may be implanted in other positions in the heart. For example, device 100 illustrated in FIGS. 1A-1K may be implanted so as to shunt blood from the right atrium to the left atrium, thus decreasing right atrial pressure; such a feature may be useful for treating a high right atrial pressure that occurs in pulmonary hypertension. Similarly, device 100 may be implanted across the ventricular septum, in an orientation suitable to shunt blood from the left ventricle to the right ventricle, or in an orientation suitable to shunt blood from the right ventricle to the left ventricle. The appended claims are intended to cover all such changes and modifications that fall within the true spirit and scope of the invention.

What is claimed is:

1. A device for regulating blood pressure between a patient's left atrium and right atrium to treat a cardiovascular condition, the device comprising:
    a stent comprising a first flared end region, a second flared end region, a neck region disposed between the first and second flared end regions and configured to engage a fossa ovalis of the patient's atrial septum, and a passageway extending from an inlet of the first flared end region through the neck region and out an outlet of the second flared end region, the stent configured to shunt blood between the left atrium and the right atrium;
    a biocompatible material disposed on the stent to define a continuous sheath that channels blood flow through the passageway; and
    a biodegradable material disposed on the device adjacent to the inlet of the first flared end region or the outlet of the second flared end region or both, the biodegradable material configured to inhibit tissue overgrowth across the biodegradable material and into the passageway of the stent.

2. The device of claim 1, wherein the stent comprises a plurality of rings interconnected by a plurality of longitudinally extending struts.

3. The device of claim 2, wherein at least one of the plurality of rings of the stent comprises one or more depressions formed on a surface of the at least one of the plurality of rings, and wherein the biodegradable material is disposed within the one or more depressions.

4. The device of claim 1, wherein the biocompatible material is disposed in the neck region, the second flared end region, and a portion of the first flared end region of the stent.

5. The device of claim 1, wherein the biocompatible material comprises ultra-high-molecular-weight-polyethylene (UHMWPE), expanded-polytetrafluoroethylene (ePTFE), polyurethane, DACRON (polyethylene terephthalate), silicone, polycarbonate urethane, or pericardial tissue from an equine, bovine, or porcine source, or any combination thereof.

6. The device of claim 1, wherein the biodegradable material comprises at least one of collagen-terpolymer, polylactic acid (PLA), poly L-lactic acid (PLLA), polyglycolic acid (PGA), poly(lactic-co-glycolic) acid copolymer (PLGA), poly(ε-caprolactone), methacrylated dextran-aminoethyl methacrylate copolymer (Dex-MA/AEMA), polydiaxanone, poly(glycerol sebacate) (PGS), polysialic acid (PSA), collagen type I/III chitosan, or chitin, or any combination thereof.

7. The device of claim 1, wherein the biodegradable material comprises a drug deposited within the biodegradable material, the drug configured to inhibit tissue overgrowth, and wherein the biodegradable material is configured to biodegrade after implantation to release the drug such that tissue overgrowth is inhibited across the biodegradable material.

8. The device of claim 7, wherein the drug comprises an "-olimus" drug such as rapamycin.

9. The device of claim 7, wherein the biocompatible material comprises a first biocompatible material layer and a second biocompatible material layer, and wherein the biodegradable material is sandwiched between the first and second biocompatible material layers, at least one of the first or second biocompatible material layers comprising a plurality of nodal pores sized and shaped to permit the drug to be released via the plurality of nodal pores as the biodegradable material biodegrades.

10. The device of claim 7, wherein the biodegradable material comprises a first biodegradable layer having a first concentration of the drug, and a second biodegradable layer having a second concentration of the drug, the second concentration of the drug different from the first concentration of the drug.

11. The device of claim 1, wherein the biodegradable material comprises one or more biodegradable rings disposed on a surface of the biocompatible material adjacent to at least the inlet of the first flared end region or the outlet of the second flared end region, the one or more biodegradable rings configured to inhibit tissue overgrowth across the one or more biodegradable rings.

12. The device of claim 11, wherein the biocompatible material comprises one or more cavities extending through a surface of the biocompatible material, and wherein the one or more biodegradable rings are disposed within the one or more cavities.

13. The device of claim 1, wherein the biodegradable material comprises a first biodegradable layer having a first biodegradable rate, and a second biodegradable layer having a second biodegradable rate, the second biodegradable rate different from the first biodegradable rate.

14. The device of claim 1, further comprising a biodegradable substance layer disposed on the biocompatible material at an inner surface of the neck region to define a cross-sectional area of a blood flow path, the biodegradable substance layer configured to biodegrade after implantation to increase the cross-sectional area of the blood flow path at the neck region over time.

15. The device of claim 14, wherein the biodegradable substance layer is configured to biodegrade after implantation to increase the diameter of the blood flow path cross-sectional area at the neck region from an initial diameter of 5 mm to a diameter of 6 mm over at least a month.

16. The device of claim 14, wherein the biodegradable substance layer is configured to biodegrade responsive to application of an external stimulus.

17. The device of claim 16, wherein the external stimulus is heat.

18. The device of claim 16, wherein the external stimulus is a biocompatible degradation activating material.

19. The device of claim 16, wherein the biodegradable substance layer comprises a first biodegradable substance layer configured to biodegrade responsive to application of a first external stimulus, and a second biodegradable substance layer configured to biodegrade responsive to application of a second external stimulus different from the first external stimulus.

20. A method of treating a subject with a cardiovascular condition, the subject having a heart with an atrial septum having a fossa ovalis therein, the method comprising:
selecting a stent comprising a neck region between first and second flared end regions and a passageway extending from an inlet of the first flared end region through the neck region and out an outlet of the second flared end region, the stent further comprising a biocompatible material disposed on the stent and a biodegradable material disposed on the biocompatible material adjacent to the inlet of the first flared end region or the outlet of the second flared end region or both;
deploying the stent at a puncture through the fossa ovalis such that the neck region is positioned in the puncture, the first flared end region is disposed in the right atrium, and the second flared end region is disposed in the left atrium;
shunting blood between the left atrium and the right atrium through the passageway; and
inhibiting tissue overgrowth into the passageway of the stent using the biodegradable material.

21. The method of claim 20, wherein the biodegradable material comprises a drug deposited within the biodegradable material, the drug configured to inhibit tissue overgrowth, and wherein the inhibiting comprises biodegrading the biodegradable material to release the drug.

22. The method of claim 21, wherein the biocompatible material comprises a first biocompatible material layer and a second biocompatible material layer, at least one of the first or second biocompatible material layers comprising a plurality of nodal pores, wherein the biodegradable material is sandwiched between the first and second biocompatible material layers, and wherein the inhibiting comprises biodegrading the biodegradable material to release the drug through the plurality of nodal pores.

23. The method of claim 20, wherein the biodegradable material comprises one or more biodegradable rings disposed on a surface of the biocompatible material adjacent to at least the inlet of the first flared end region or the outlet of the second flared end region, and wherein the inhibiting comprises biodegrading the one or more biodegradable rings.

24. The method of claim 20, wherein the biodegradable material comprises a first biodegradable layer having a first biodegradable rate, and a second biodegradable layer having a second biodegradable rate, the second biodegradable rate different from the first biodegradable rate, and wherein the inhibiting comprises biodegrading the first biodegradable layer at the first biodegradable rate and biodegrading the second biodegradable layer at the second biodegradable rate.

25. The method of claim 20, wherein the stent further comprises a biodegradable substance layer disposed on the biocompatible material at an inner surface of the neck region, the method further comprising biodegrading the biodegradable substance layer after implantation to increase a cross-sectional area at the neck region.

* * * * *